US012289989B2

(12) United States Patent
Zhang et al.

(10) Patent No.: US 12,289,989 B2
(45) Date of Patent: Apr. 29, 2025

(54) COMPOUND, DISPLAY PANEL, AND DISPLAY DEVICE

(71) Applicant: Shanghai Tianma AM-OLED Co., Ltd., Shanghai (CN)

(72) Inventors: Lei Zhang, Shanghai (CN); Wei Gao, Shanghai (CN); Jinghua Niu, Shanghai (CN); Wenpeng Dai, Shanghai (CN); Wenjing Xiao, Shanghai (CN); Xia Li, Shanghai (CN)

(73) Assignees: WUHAN TIANMA MICRO-ELECTRONICS CO., LTD., Wuhan (CN); WUHAN TIANMA MICROELECTRONICS CO., LTD. SHANGHAI BRANCH, Shanghai (CN)

( * ) Notice: Subject to any disclaimer, the term of this patent is extended or adjusted under 35 U.S.C. 154(b) by 551 days.

(21) Appl. No.: 16/719,733

(22) Filed: Dec. 18, 2019

(65) Prior Publication Data

US 2021/0098705 A1   Apr. 1, 2021

(30) Foreign Application Priority Data

Sep. 26, 2019   (CN) .......................... 201910917798.9

(51) Int. Cl.
*H10K 85/60*   (2023.01)
*C07D 307/91*   (2006.01)
(Continued)

(52) U.S. Cl.
CPC ......... *H10K 85/636* (2023.02); *C07D 307/91* (2013.01); *C07D 405/04* (2013.01);
(Continued)

(58) Field of Classification Search
CPC .. C07D 403/04; C07D 405/04; C07D 407/04; C07D 409/04; C07D 307/91;
(Continued)

(56) References Cited

U.S. PATENT DOCUMENTS

2017/0301868 A1* 10/2017 Lee ...................... C07D 209/82
2019/0341552 A1* 11/2019 Wu ...................... H01L 51/0061
2022/0127251 A1*  4/2022 Ehrenreich ........... C07C 217/84

FOREIGN PATENT DOCUMENTS

CN   108623545 A   10/2018
CN   109232277 A    1/2019
(Continued)

OTHER PUBLICATIONS

CN-108623545-A, 2018, machine translation (Year: 2018).*
(Continued)

*Primary Examiner* — Elizabeth M. Dahlburg
(74) *Attorney, Agent, or Firm* — CHRISTENSEN O'CONNOR JOHNSON KINDNESS PLLC

(57) ABSTRACT

The present disclosure belongs to technical field of OLEDs, and provides a compound suitable as a hole transport material and an electron blocking material of OLEDs. The compound has a general structure according to [Chemical Formula 1], in which $Ar_1$ and $Ar_2$ are each independently selected from a hydrogen atom, a substituted or unsubstituted C5-C40 aryl, or a substituted or unsubstituted C5-C40 heteroaryl; m and n are each an integer independently selected from 0, 1, or 2; X is selected from O, S, or —NR—; R is selected from hydrogen, or a substituted or unsubstituted C5-C40 aryl; $Ar_3$ has a structure according to [Chemical Formula 2], in which $R_1$-$R_8$ are each independently selected from a hydrogen atom, or a substituted or unsubstituted C5-C40 aryl; Y is selected from O, S, or —NR'—; and R' is selected from a hydrogen atom, or a substituted or unsubstituted C5-C40 aryl.

(Continued)

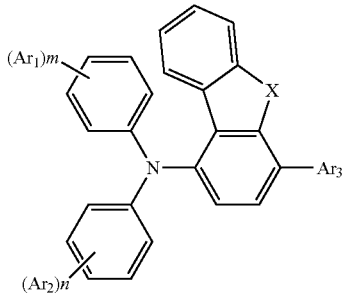

[Chemical Formula 1]

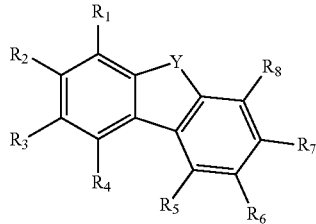

[Chemical Formula 2]

10 Claims, 2 Drawing Sheets

(51) Int. Cl.
    *C07D 405/04* (2006.01)
    *C07D 409/14* (2006.01)
    *H10K 50/15* (2023.01)
    *H10K 50/18* (2023.01)
    *H10K 101/30* (2023.01)

(52) U.S. Cl.
    CPC ............ *C07D 409/14* (2013.01); *H10K 50/15* (2023.02); *H10K 50/18* (2023.02); *H10K 85/654* (2023.02); *H10K 85/6572* (2023.02); *H10K 85/6574* (2023.02); *H10K 85/6576* (2023.02); *H10K 2101/30* (2023.02)

(58) Field of Classification Search
CPC .. C07D 409/14; C07D 401/14; C07D 405/14; C07D 209/86; C07D 403/14; H01L 51/0061; H01L 51/0071; H01L 51/0072; H01L 51/0073; H01L 51/0074; H01L 51/5004; H01L 51/5048; H01L 51/5052; H01L 51/5056; H01L 51/506; H01L 51/5064; H01L 51/5088; H01L 50/96; H01L 2251/55; H01L 2251/552; H10K 85/631; H10K 85/636; H10K 85/654; H10K 85/657; H10K 85/6572; H10K 85/6574; H10K 85/6576; H10K 50/11; H10K 50/14; H10K 50/15; H10K 50/155; H10K 50/156; H10K 50/17; H10K 50/18; H10K 2101/30; H10K 2101/40; H10K 50/181
See application file for complete search history.

(56) References Cited

FOREIGN PATENT DOCUMENTS

| | | | | |
|---|---|---|---|---|
| CN | 110526887 A | 12/2019 | | |
| EP | 0721935 A1 | 7/1996 | | |
| KR | 2014130297 A | * | 11/2014 | ........... C07D 487/04 |
| KR | 1535606 B1 | * | 7/2015 | ........... C07D 209/82 |
| KR | 20190020514 A | 3/2019 | | |
| WO | WO-2017196081 A1 | * | 11/2017 | ........... C07D 209/82 |
| WO | 2020007770 A1 | 1/2020 | | |

OTHER PUBLICATIONS

Office Action, dated Jun. 11, 2020, for Chinese Patent Application No. 201910917798.9. (with English translation, 18 pages).

* cited by examiner

COMPOUND, DISPLAY PANEL, AND DISPLAY DEVICE

CROSS-REFERENCE TO RELATED APPLICATIONS

The present application claims priority to Chinese Patent Application No. 201910917798.9, filed on Sep. 26, 2019, the content of which is incorporated herein by reference in its entirety.

TECHNICAL FIELD

The present disclosure relates to the technical field of organic light emitting diodes (OLEDs), and particularly, to a compound suitable for use as a hole transport material and an electron blocking material, and a display panel and a display device including the compound.

BACKGROUND

Many small- or medium-sized OLED screens such as mobile phone consumer products adopt R, G, B sub-pixel display mode. In order to improve the production yield, some functional layers are usually designed as common layers in order to reduce the use of fine metal mask (FMM), while a hole transport layer often uses a common layer, and the common hole transport layer can be made of a commercially available material.

Existing hole transport materials have multiple problems: the solubility is poor, which may result in a unsatisfying cleaning effect of an evaporation mask during mass production; mobility of some materials is too slow, thereby leading to an excessively high overall voltage of light-emitting devices; mobility, particularly the lateral mobility of some materials, is too fast, thereby causing crosstalk between adjacent pixels; a LUMO energy level of the materials is too deep to effectively block electron migration that may cross over a light-emitting layer; and a triplet energy level of the materials is too low to achieve effective transport of holes in the RGB three colors synchronously, thereby resulting in an increase in the number of masks used and an increase in process difficulty.

In European patent application EP-721935, commercially available materials have mobility in an acceptable range without occurrence of crosstalk, but have a poor solubility and low triplet energy level, and thus they are unlikely to be applied to OLED elements.

SUMMARY

A first aspect of the present disclosure provides a compound having a general structure according to [Chemical Formula 1], in which $Ar_1$ and $Ar_2$ are each independently selected from the group consisting of a hydrogen atom, a substituted or unsubstituted C5-C40 aryl, and a substituted or unsubstituted C5-C40 heteroaryl; m and n are each an integer independently selected from 0, 1, or 2; X is selected from the group consisting of O, S, and —NR—; R is selected from a hydrogen atom, or a substituted or unsubstituted C5-C40 aryl; and $Ar_3$ has a structure according to [Chemical Formula 2], in which $R_1$-$R_8$ are each independently selected from the group consisting of a hydrogen atom, and a substituted or unsubstituted C5-C40 aryl; Y is selected from the group consisting of O, S, and —NR'—; and R' is selected from the group consisting of a hydrogen atom, and a substituted or unsubstituted C5-C40 aryl.

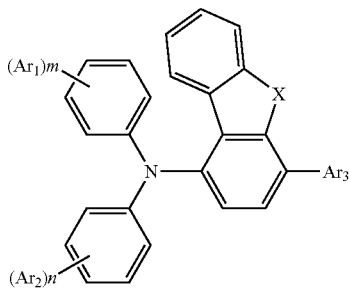

[Chemical Formula 1]

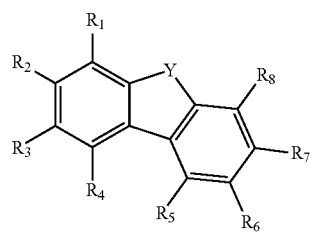

[Chemical Formula 2]

A second aspect of the present disclosure provides a display panel including an organic light-emitting element, the organic light-emitting element includes an anode, a cathode arranged opposite to the anode, a hole transport layer, and a light-emitting layer, wherein the hole transport layer and the light-emitting layer are disposed between the anode and the cathode, and a material of the hole transport layer comprises one or more compounds of the first aspect.

A third aspect of the present disclosure provides a display device including the display panel of the second aspect.

DESCRIPTION OF EMBODIMENTS

The present disclosure is further described in combination with the following examples and comparative examples. These examples are merely used to illustrate the present disclosure and the present disclosure is not limited to the following examples. Without departing from the scope of technical solutions of the present disclosure, modifications or equivalent substitutions of the technical solutions of the present disclosure should be included in the protection scope of the present disclosure.

A first aspect of the present disclosure provides a compound having a general structure according to [Chemical Formula 1]:

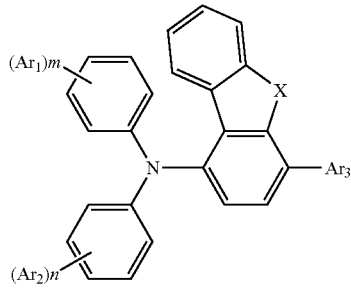

[Chemical Formula 1]

in which, Ar$_1$ and Ar$_2$ are each independently selected from the group consisting of a hydrogen atom, a substituted or unsubstituted C5-C40 aryl, and a substituted or unsubstituted C5-C40 heteroaryl; m and n are each an integer independently selected from 0, 1, and 2;

X is selected from the group consisting of O, S, and —NR—; and R is selected from the group consisting of a hydrogen atom, and a substituted or unsubstituted C5-C40 aryl;

Ar$_3$ has a structure according to [Chemical Formula 2]:

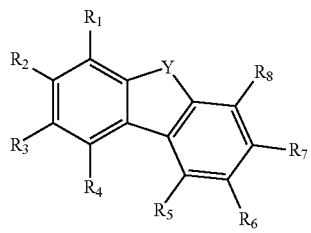

[Chemical Formula 2]

R$_1$-R$_8$ are each independently selected from the group consisting of a hydrogen atom, a substituted or unsubstituted C5-C40 aryl; Y is selected from the group consisting of O, S, and —NR'—; and R' is selected from the group consisting of a hydrogen atom, and a substituted or unsubstituted C5-C40 aryl.

Figure 1:
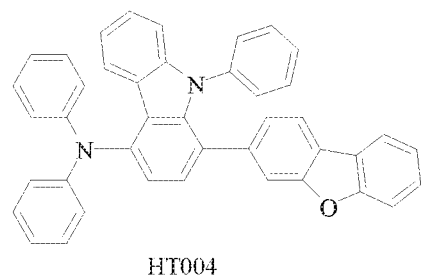
FIG. 1 is a chemical structure of an exemplary compound HT004 of the present disclosure.

FIG. 1 shows an exemplary compound of the present disclosure. A hole transport material containing the above compound not only has a triarylamine group which is also included in conventional hole transport materials, but also has a LUMO energy level that can be adjusted. In addition, the hole transport material contains relatively weak electron-donating groups. These weak electron-donating groups impart the molecule with a higher HOMO level, thereby effectively improving a hole transport capability.

According to an embodiment of the compound of the present disclosure, the compound has a structure according to [Chemical Formula 1-1]:

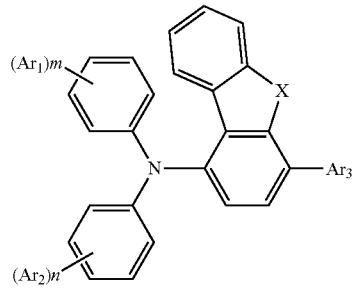

[Chemical Formula 1-1]

in which, X is O or S.

According to an embodiment of the compound of the present disclosure, the compound has a structure according to [Chemical Formula 1-2]:

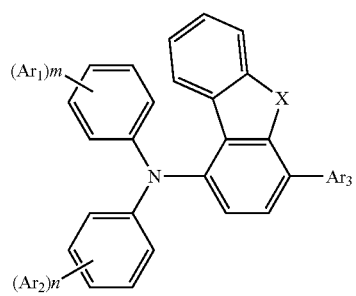

[Chemical Formula 1-2]

in which, X is —NR—, and R is a hydrogen atom or phenyl.

According to an embodiment of the compound of the present disclosure, in [Chemical Formula 1], Ar$_1$ and Ar$_2$ are each independently selected from a hydrogen atom, or phenyl.

When Ar$_1$ and Ar$_2$ are each a hydrogen atom or phenyl, synthesis of the molecules is simple. In addition, the HOMO value of the molecule can be effectively adjusted by increasing or decreasing the number of phenyl groups to match different material systems.

According to an embodiment of the compound of the present disclosure, in [Chemical Formula 1], m and n are each an integer independently selected from 0, and 1.

According to an embodiment of the compound of the present disclosure, the compound has a structure according to [Chemical Formula 1-2]:

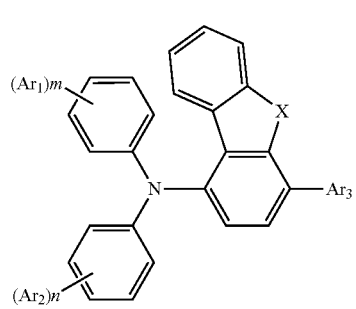

[Chemical Formula 1-2]

in which, X is —NR—; R is a hydrogen atom or phenyl; and, Ar₃ has one of the following structures:

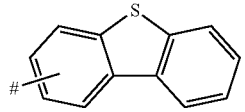
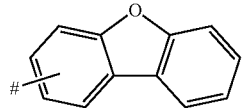

in which, # indicates a bonding position in [Chemical Formula 1].

The compound of the present embodiment has an aromatic amine structure and has good hole transport characteristics, and introduction of dibenzothiophenyl and dibenzofuryl groups adjusts the HOMO level of the molecule to match materials of other light-emitting functional layers.

According to an embodiment of the compound of the present disclosure, in [Chemical Formula 2], $R_1$-$R_8$ are each a hydrogen atom.

According to an embodiment of the compound of the present disclosure, the compound has a molecular weight smaller than or equal to 1000.

By limiting the molecular weight of the hole transport material of the present disclosure to 1000 or less, the hole transport material can have a lower melting temperature, such that the hole transport material is more suitable for evaporation.

According to an embodiment of the compound of the present disclosure, the compound is selected from the following compounds:

HT001

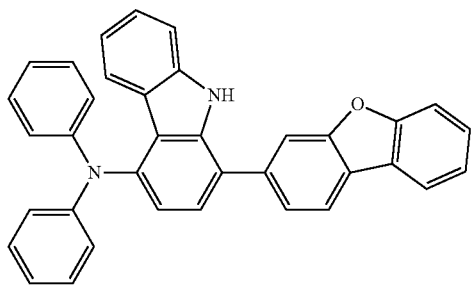

HT002

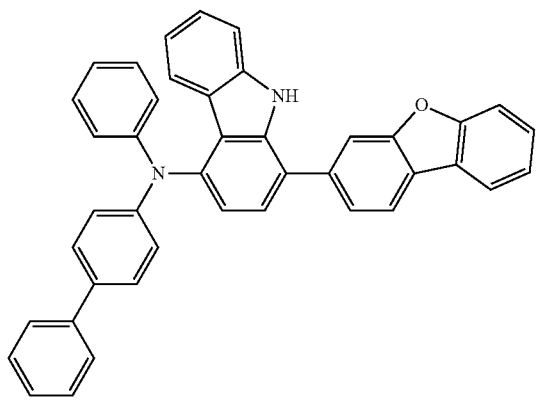

-continued

HT003

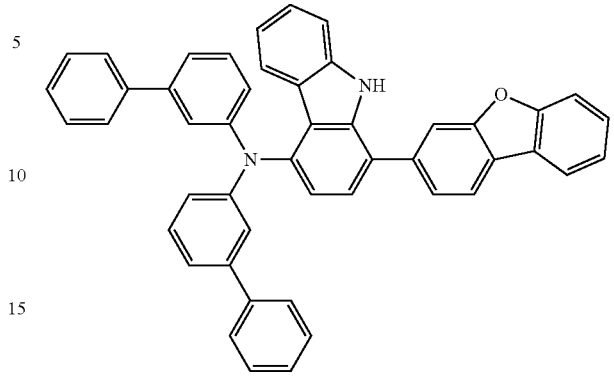

HT004

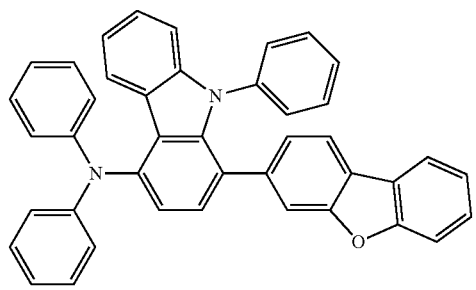

HT005

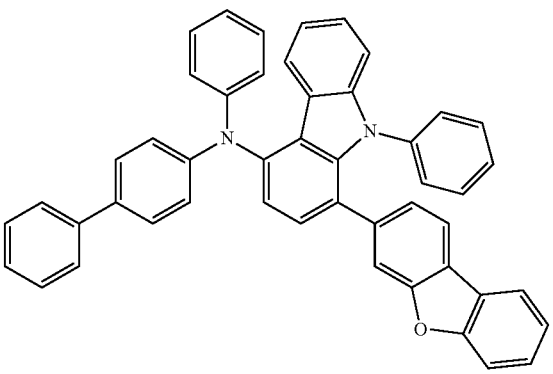

HT006

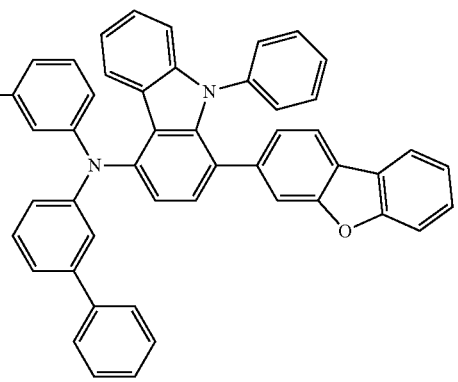

HT007
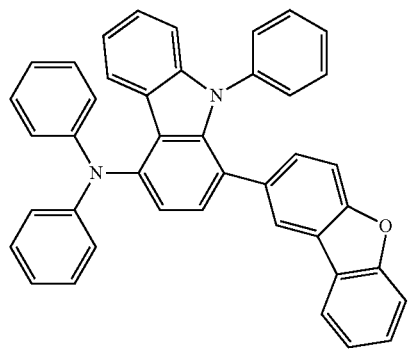
HT008
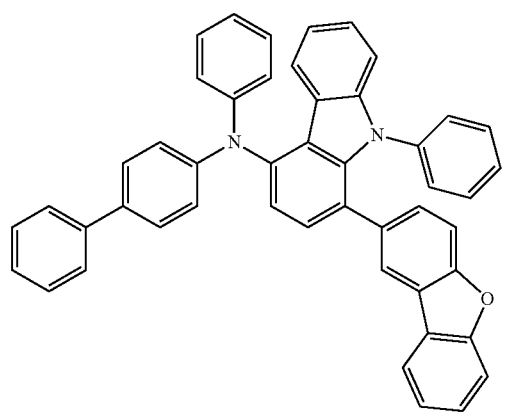
HT009
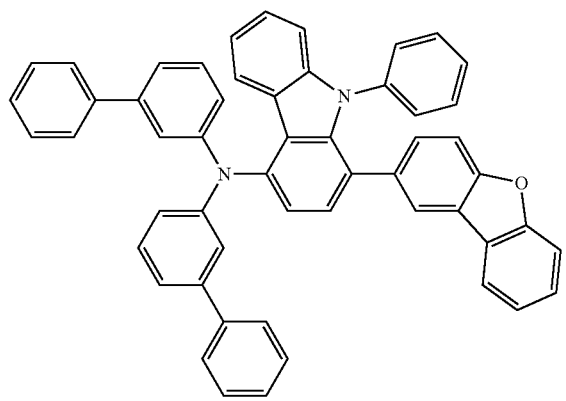
HT010
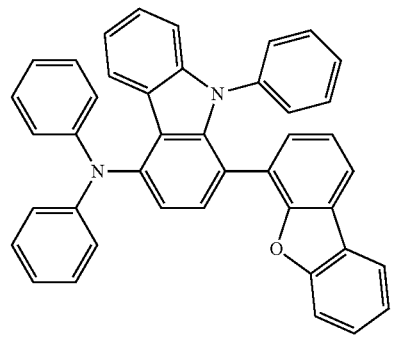
HT011
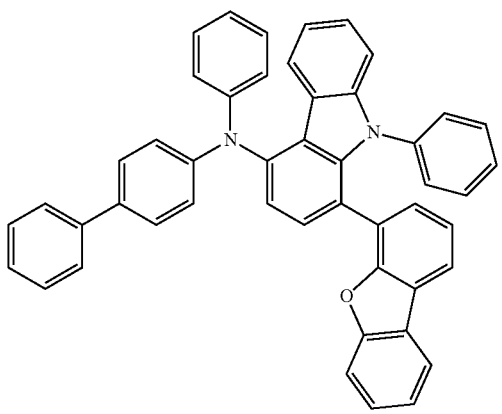
HT012
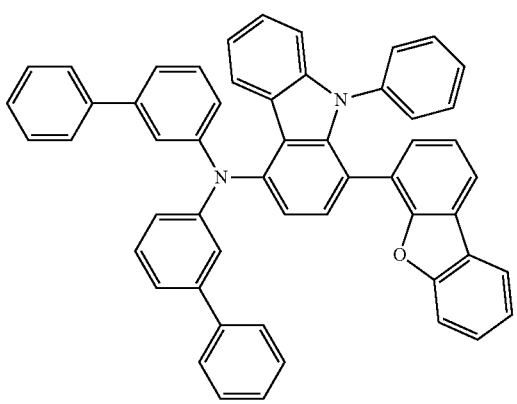
HT013
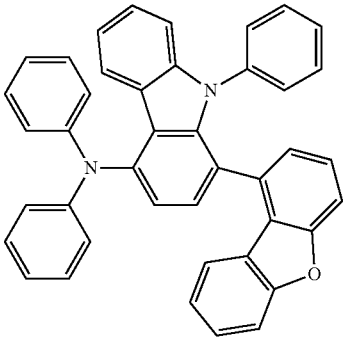
HT014
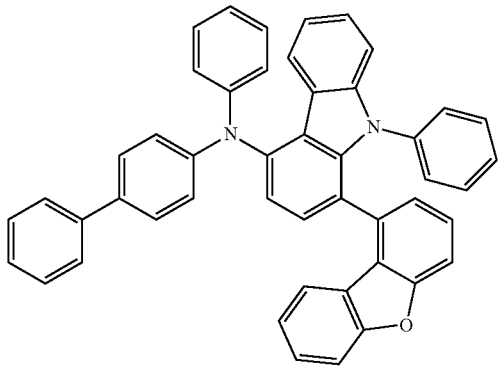

HT015
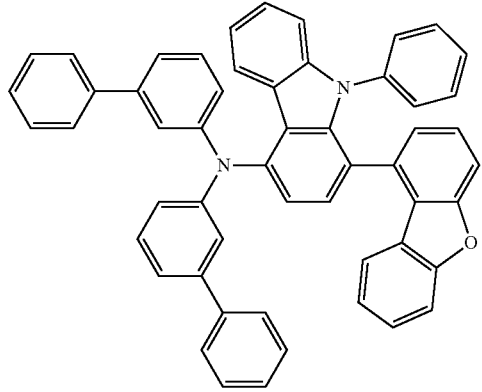
HT016
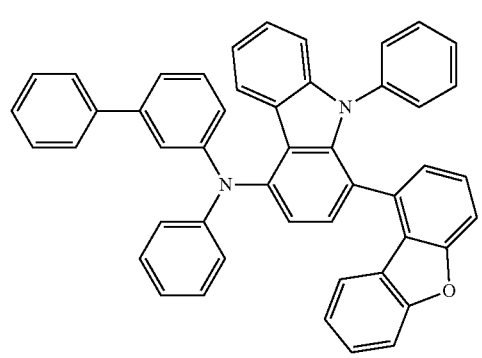
HT017
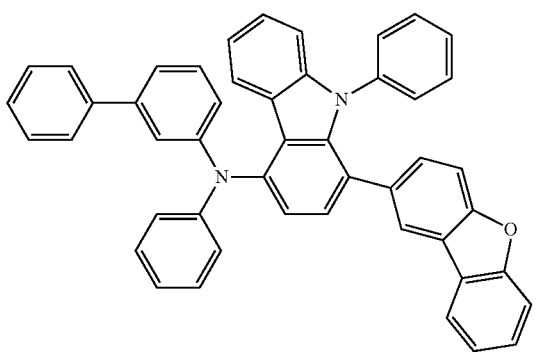
HT018
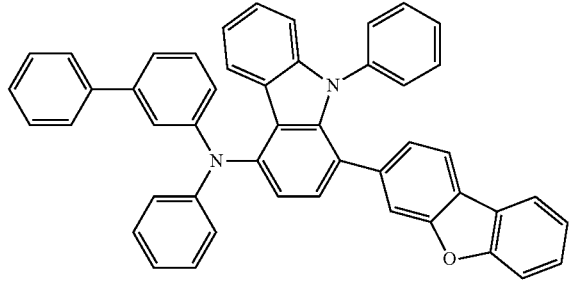
HT019
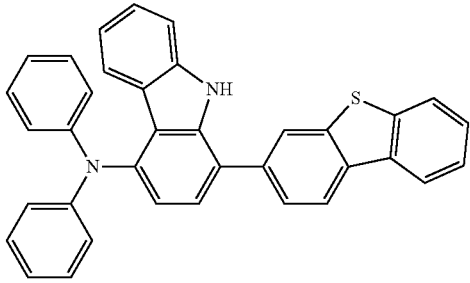
HT020
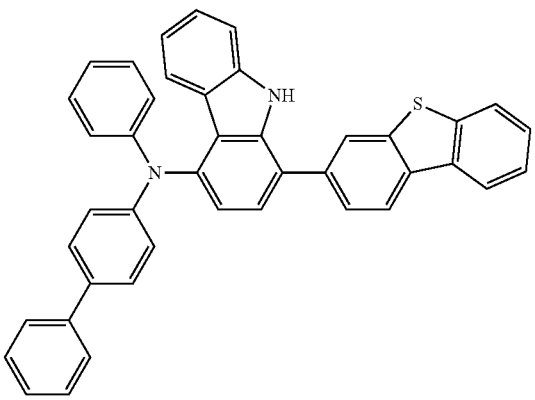
HT021
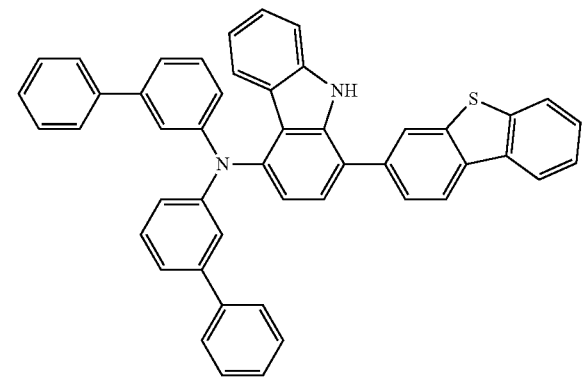
HT022
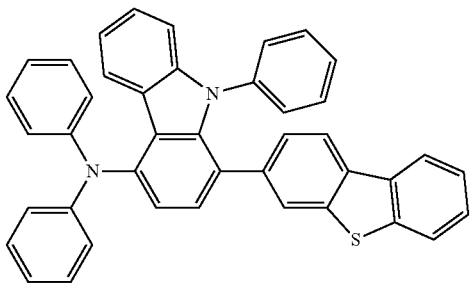

HT023
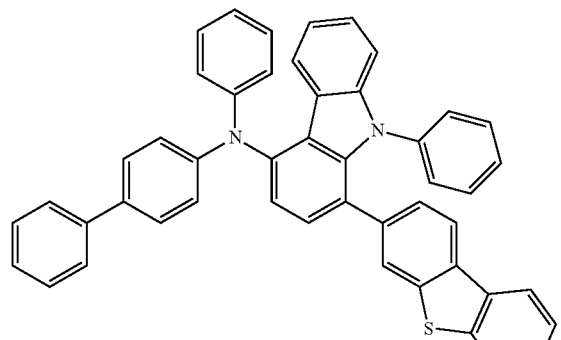
HT024
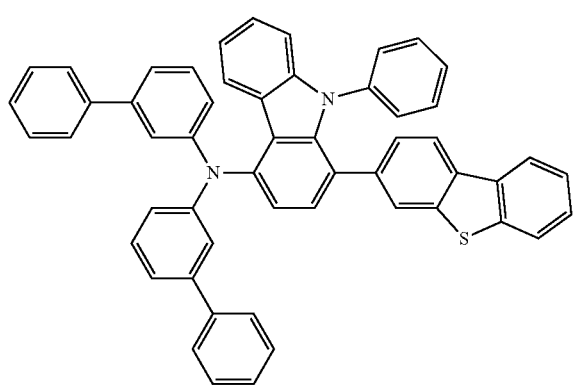
HT025
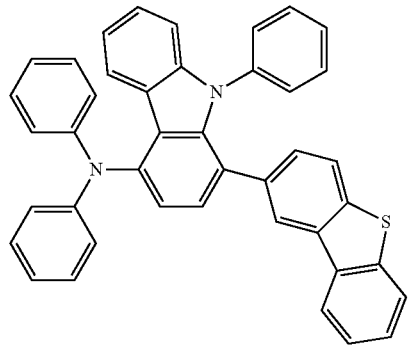
HT026
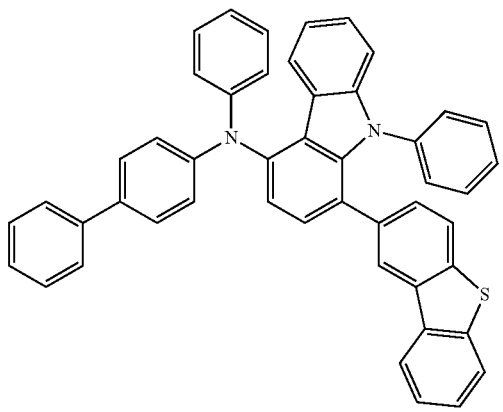
HT027
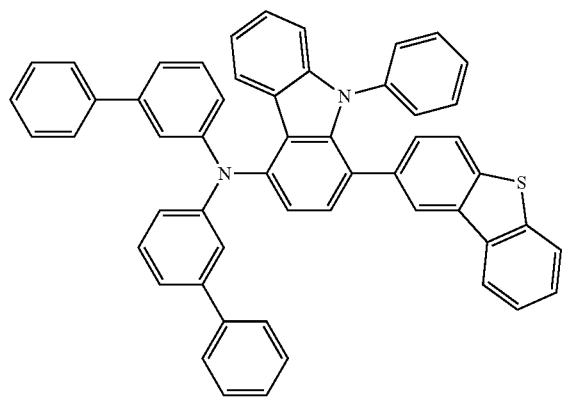
HT028
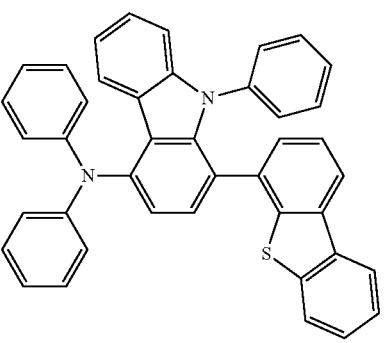
HT029
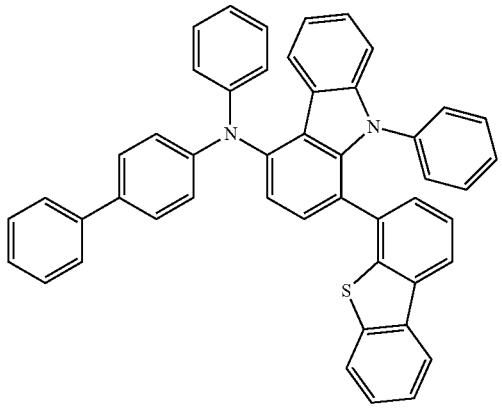
HT030
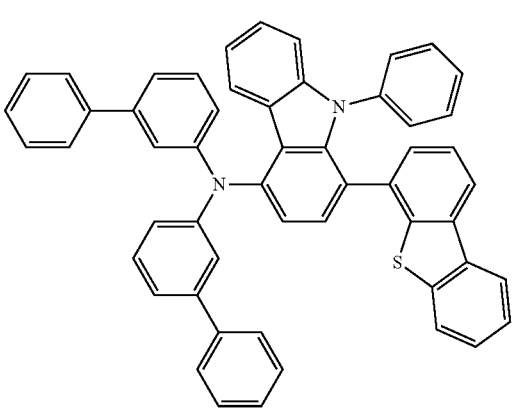

HT031
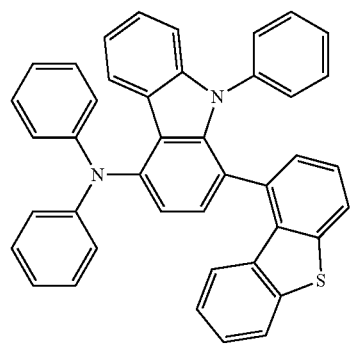
HT032
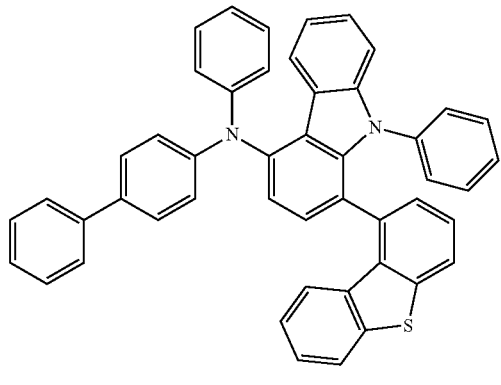
HT033
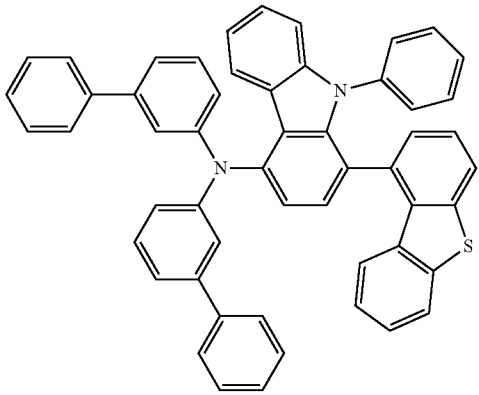
HT034
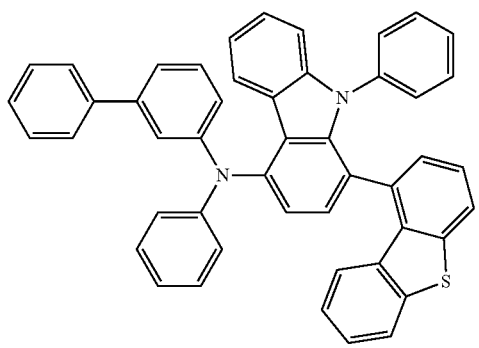
HT035
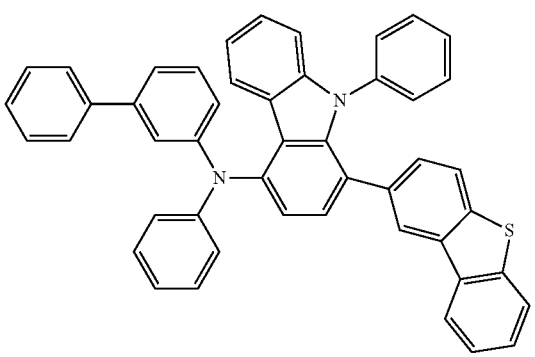
HT036
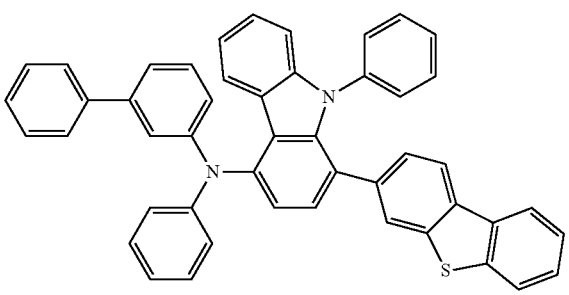
HT037
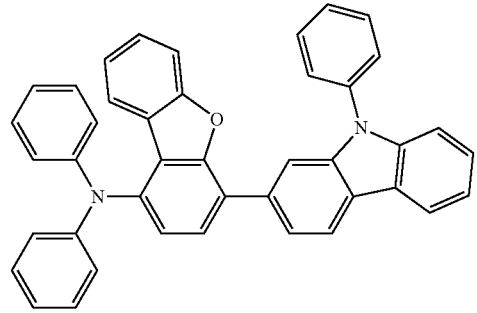
HT038
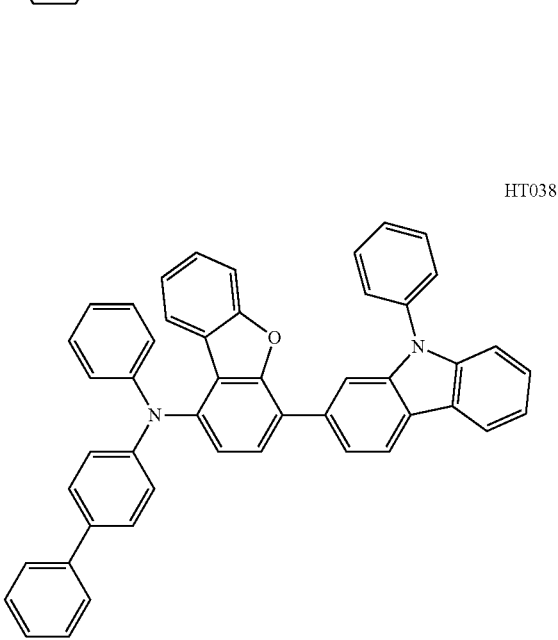

HT039
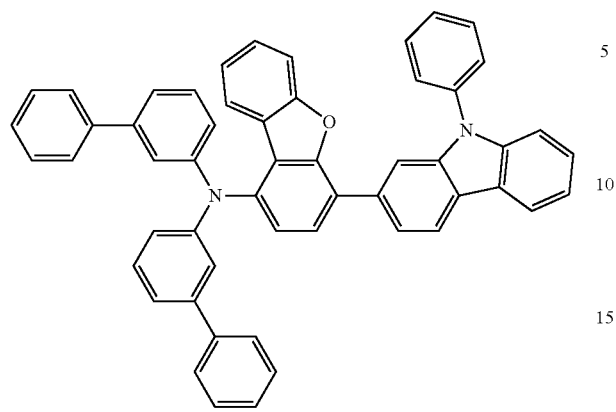
HT040
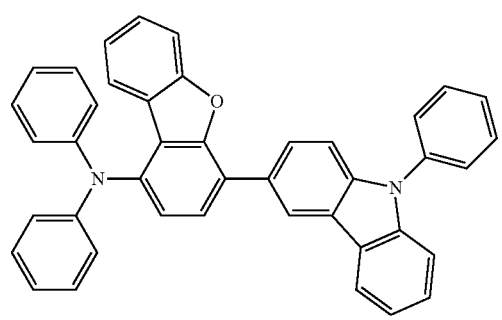
HT041
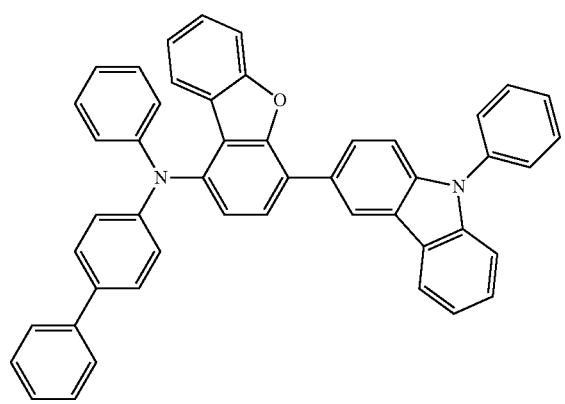
HT042
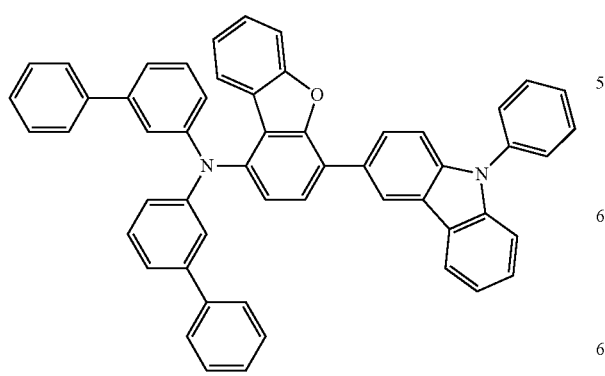
HT043
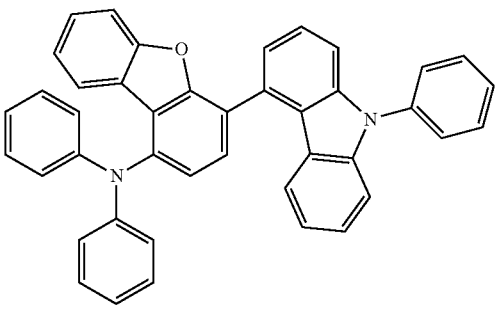
HT044
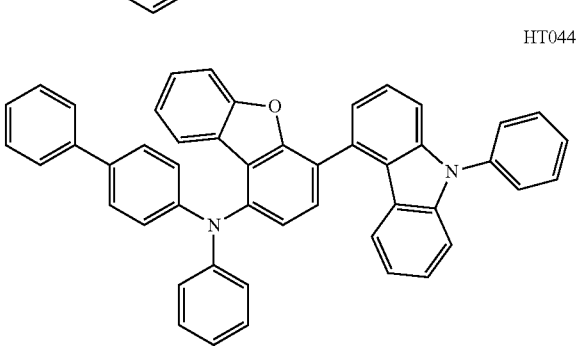
HT045
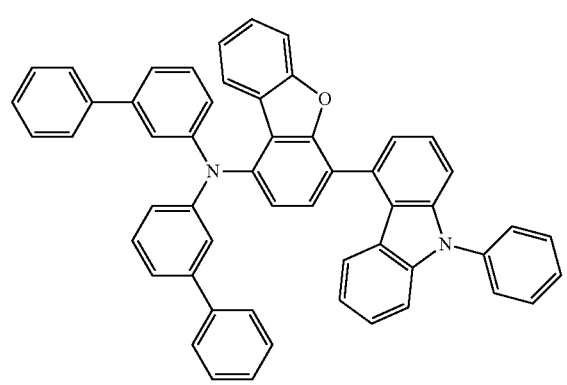
HT046
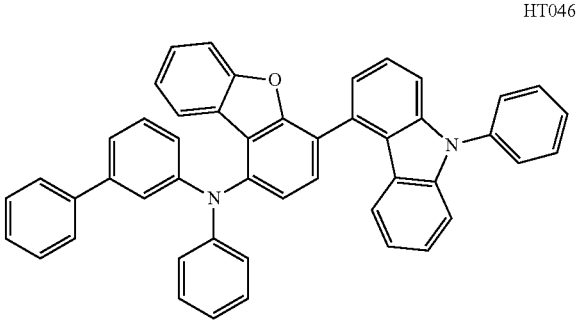

HT047
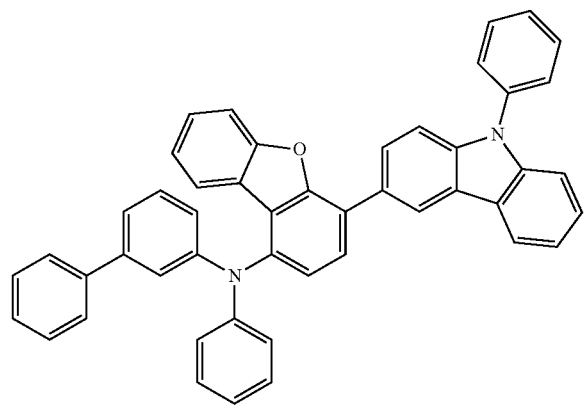
HT048
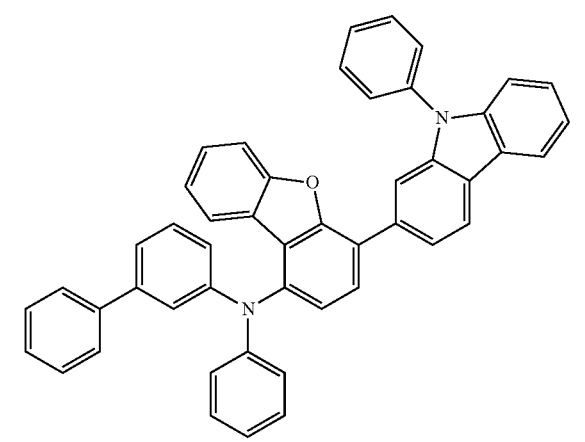
HT049
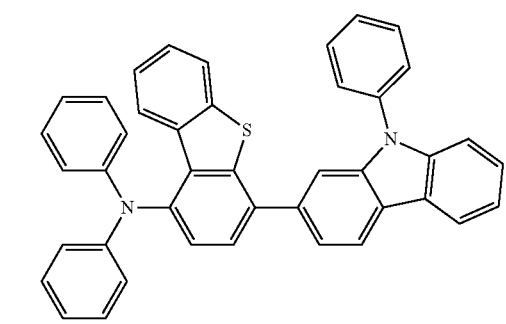
HT050
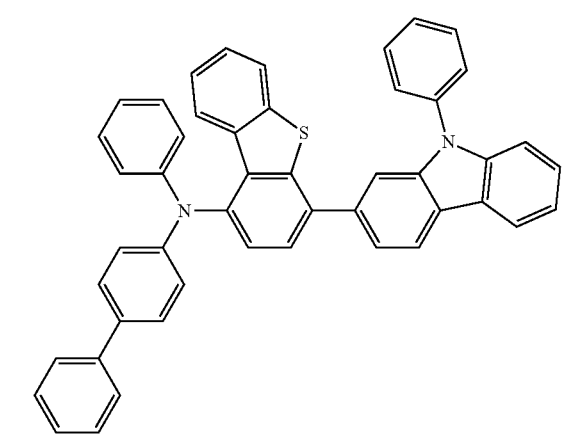
HT051
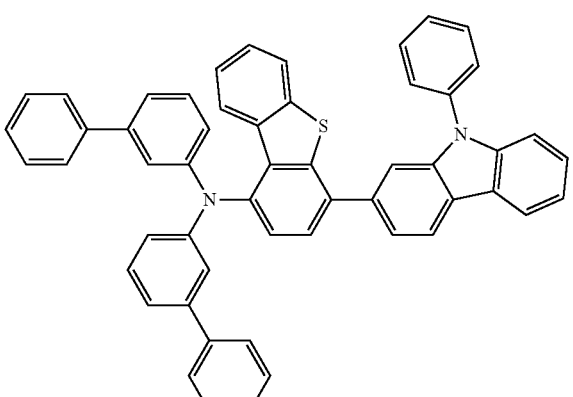
HT052
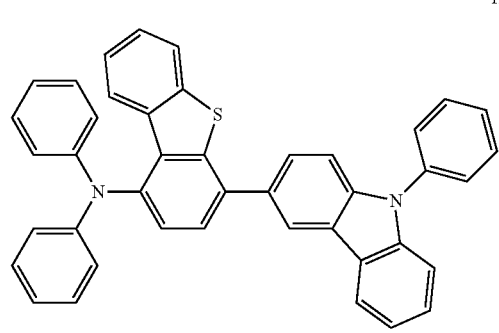
HT053
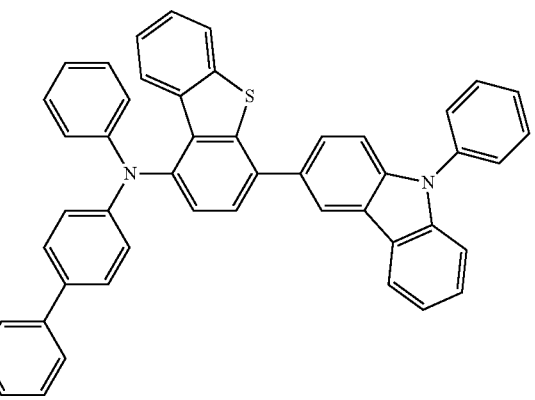
HT054
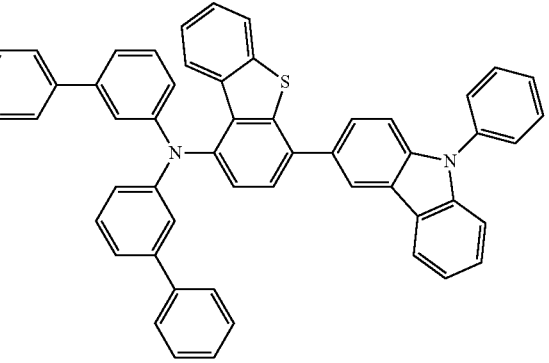

HT055
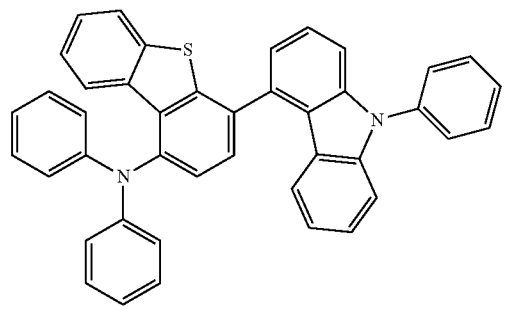
HT056
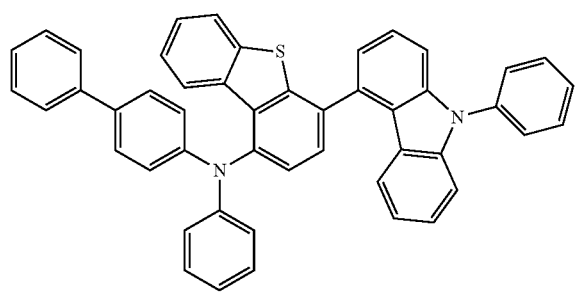
HT057
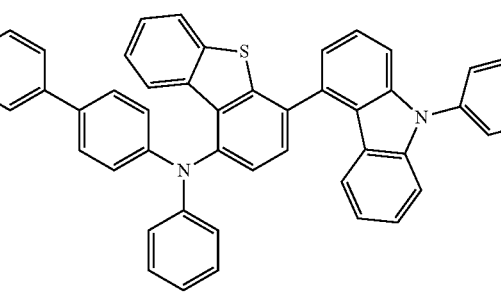
HT058
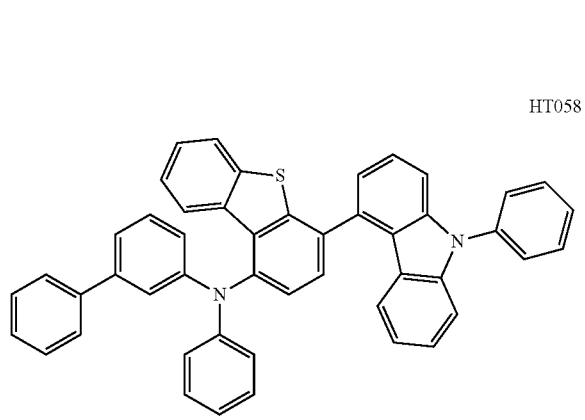
HT059
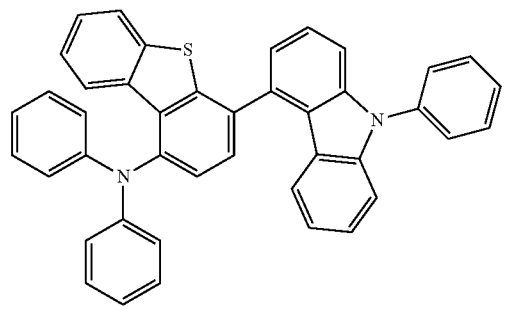
HT060
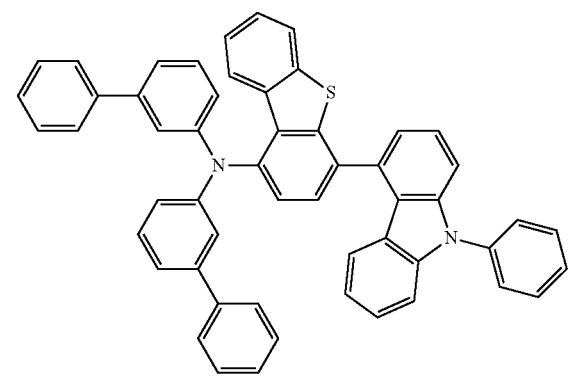
HT061
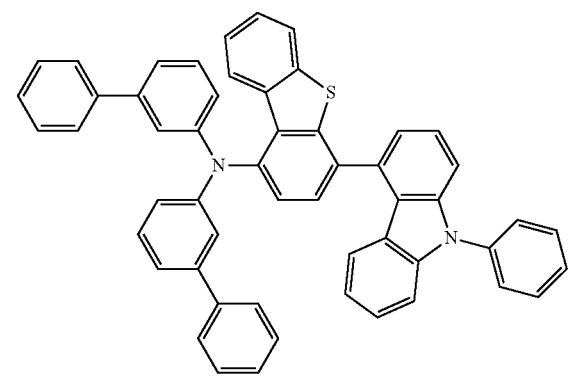
HT062
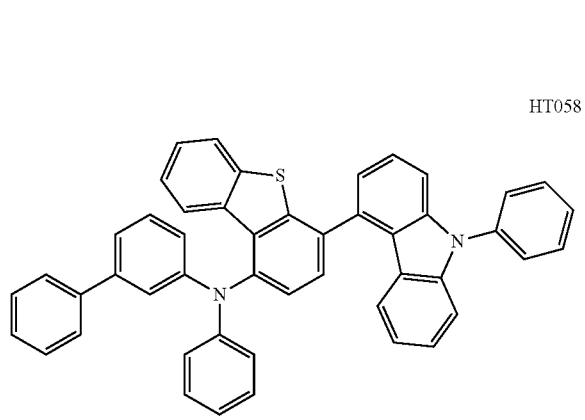

HT063
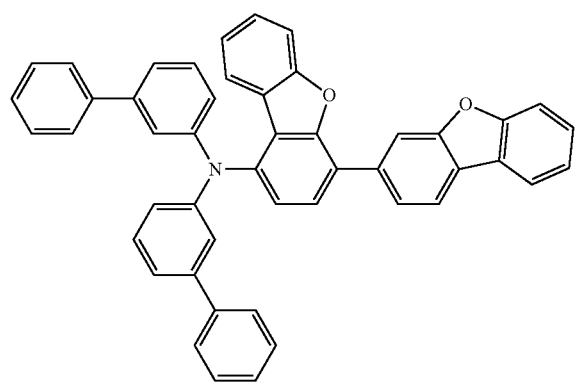
HT064
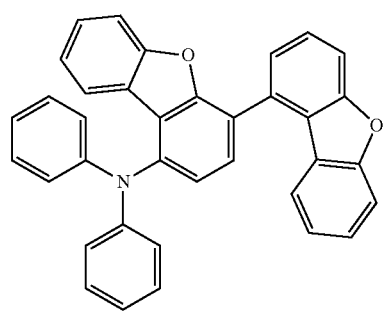
HT065
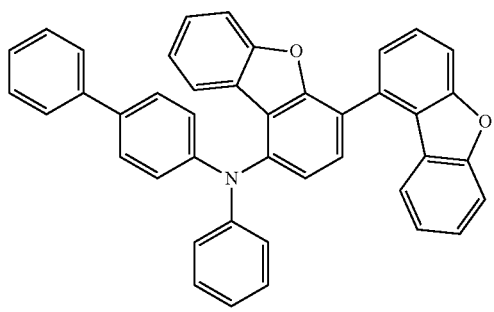
HT066
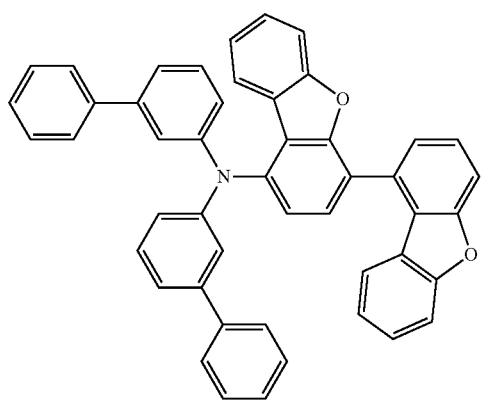
HT067
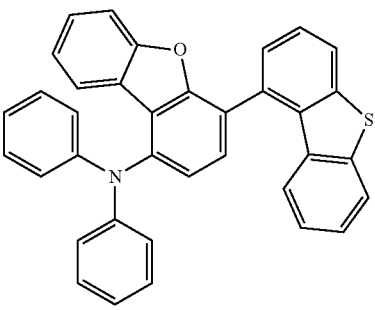
HT068
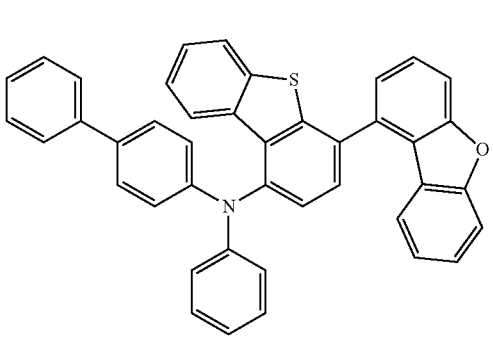
HT069
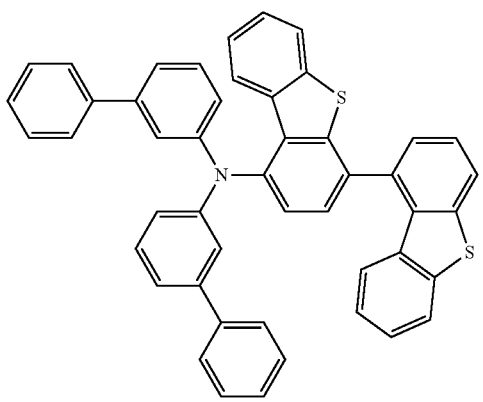
HT070
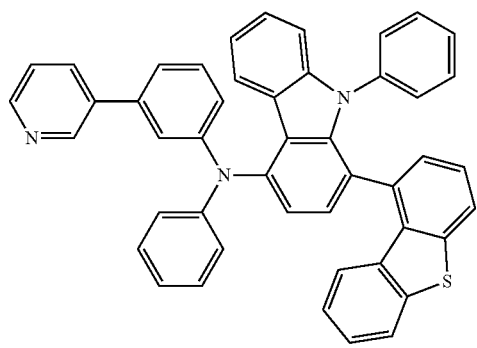

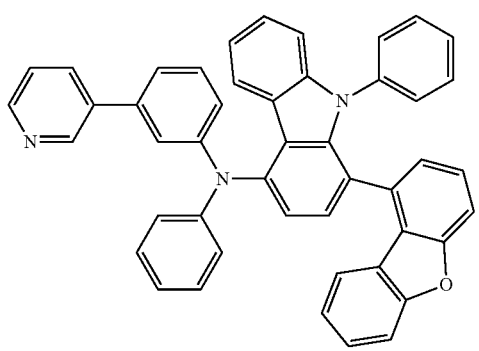

HT071

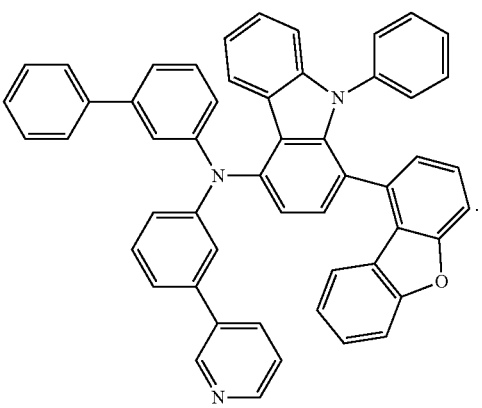

HT072

According to an embodiment of the present disclosure, the compound has a triplet energy level $E_T$ greater than or equal to 2.6 eV. The compound of the present disclosure has a high triplet energy level, which is suitable to block transport of excitons, confine the excitons to the light-emitting layer, and prevent or limit exciton loss, thereby improving a light-emitting efficiency of an organic light-emitting element including one or more compositions of the present disclosure.

According to an embodiment of the present disclosure, the compound has a glass transition temperature $T_g$ greater than or equal to 120° C., having high heat resistance and stability, such that the material of the present disclosure is more suitable to be used in mass production.

The present disclosure further provides a display panel including an organic light-emitting element, the organic light-emitting element includes an anode, a cathode arranged opposite to the anode, a hole transport layer, and a light-emitting layer, the hole transport layer and the light-emitting layer are disposed between the anode and the cathode, and a material of the hole transport layer comprises one or more compounds described in the present disclosure.

In the display panel according to the present disclosure, the display panel further includes an electron blocking layer disposed between the anode and the cathode, and the electron blocking layer includes one or more compounds described in the present disclosure.

In the organic light-emitting element provided by the present disclosure, in an embodiment, the anode comprises a material selected from metals, such as metals selected from the group consisting of copper, gold, silver, iron, chromium, nickel, manganese, palladium, platinum, etc., and alloys thereof. In an embodiment, the anode comprises one or more metal oxides, such as a metal oxide selected from the group consisting of indium oxide, zinc oxide, indium tin oxide (ITO), indium zinc oxide (IZO), and so on. In an embodiment, the anode comprises one or more conductive polymers, such as a conductive polymer selected from the group consisting of polyaniline, polypyrrole, poly(3-methylthiophene), and so on. In addition to the anode materials listed above, in an embodiment, the anode comprises a material selected from any materials that are conductive to hole injection, or combinations thereof, including the materials known in the related art that are suitable as the material of the anode.

In the organic light-emitting element provided by the present disclosure, in an embodiment, the cathode comprises a material selected from one or more metals, such as a metal selected from the group consisting of aluminum, magnesium, silver, indium, tin, titanium, etc., and alloys thereof. In an embodiment, the cathode comprises a multiple-layered metal material, such as a multi-layered material selected from the group consisting of LiF/Al, $LiO_2$/Al, $BaF_2$/Al, and so on. In addition to the cathode materials listed above, the cathode can also be made of a material selected from any materials that are conductive to electron injection, or combinations thereof, including the materials known in the related art that are suitable as the material of the cathode.

In an embodiment of the present disclosure, a manufacturing process of the organic light-emitting element includes: forming an anode on a transparent or opaque smooth substrate, forming an organic thin film layer on the anode, and forming a cathode on the organic thin film layer. The organic thin film layer can be formed by a known method such as vapor deposition, sputtering, spin coating, dipping, ion plating, and so on. The organic thin film layer at least includes a hole transport layer and a light-emitting layer, and the hole transport layer is made of the compound according to the present disclosure. The organic thin film layer can further includes an electron blocking layer, and the electron blocking layer is made of the compound according to the present disclosure.

Another aspect of the present disclosure describes syntheses of Compound HT007, Compound HT012, Compound HT044, Compound HT062 and Compound H070.

Example 1

Synthesis of Compound HT007

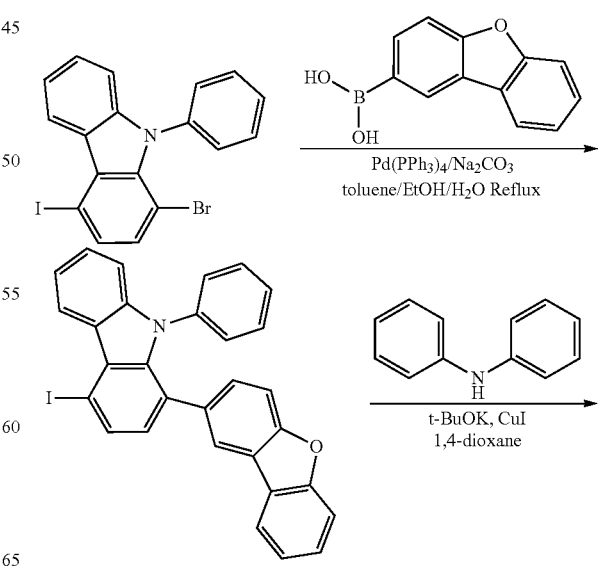

HT007-1

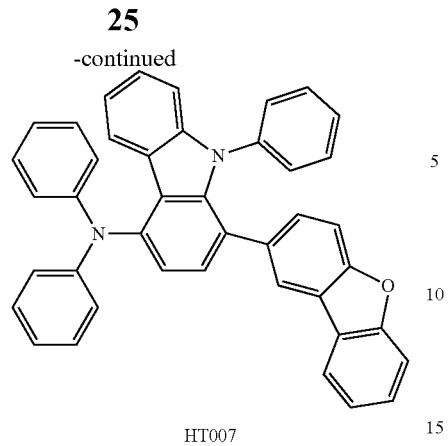

HT007

In a 250 ml round bottom flask, 1-bromo-4-iodo-9-phenyl-9H-carbazole (12 mmol), 3-dibenzofuranboronic acid (10 mmol), and Na$_2$CO$_3$ (80 mmol) were respectively added to a solvent of toluene/EtOH (anhydrous ethanol)/H$_2$O (75/25/50, mL) to obtain a mixed solution, then Pd(PPh$_3$)$_4$ (0.48 mmol) was added to the above mixed solution. An intermediate, which was obtained after reflux reaction under nitrogen atmosphere for 20 h, was cooled to room temperature, added to water, and then filtered through a diatomite pad. The filtrate was extracted with dichloromethane, then washed with water and dried over anhydrous magnesium sulfate. The crude product obtained after filtration and evaporation was purified through silica-gel column chromatography to obtain an intermediate product HT007-1.

In a 250 ml round bottom flask, the intermediate product HT007-1 (12 mmol), cuprous iodide (15 mmol), potassium t-butoxide (65 mmol), 1,2-diaminocyclohexane (12 mmol), and diarylamine (12 mmol) were added to dried 1,4-dioxane (100 ml), the mixture was refluxed for 48 hours under N$_2$ atmosphere to obtain an intermediate. The obtained intermediate was cooled to room temperature, added to water, and then filtered through a diatomite pad. The filtrate was extracted with dichloromethane, then washed with water and dried over anhydrous magnesium sulfate. The crude product obtained after filtration and evaporation was purified through silica-gel column chromatography to obtain an aimed product HT007.

Elementary analysis results of Compound HT007 (molecular formula C$_{42}$H$_{28}$N$_2$O): theoretical: C, 87.47; H, 4.89; N, 4.86; O, 2.77. Measured: C, 87.47; H, 4.88; N, 4.87; O, 2.77. ESI-MS (m/z) (M$^+$) analyzed by liquid chromatography-mass spectrometry: theoretical: 576.22; and measured: 576.68.

Example 2

Synthesis of Compound HT012

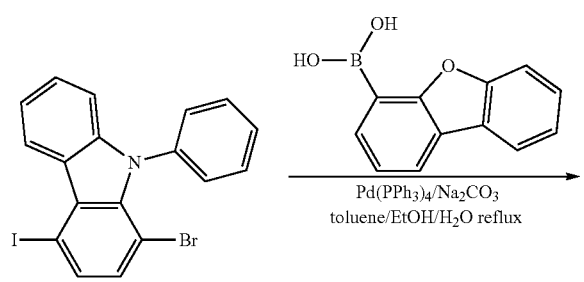

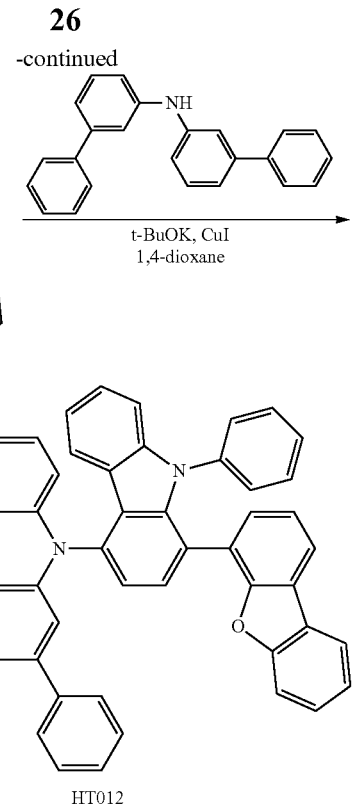

HT012-1

HT012

In a 250 ml round bottom flask, 1-bromo-4-iodo-9-phenyl-9H-carbazole (12 mmol), 1-dibenzofuranboronic acid (10 mmol) and Na$_2$CO$_3$ (80 mmol) were respectively added to a solvent of toluene/EtOH (anhydrous ethanol)/H$_2$O (75/25/50, mL) to obtain a mixed solution, then Pd(PPh$_3$)$_4$ (0.48 mmol) was added to the above mixed solution. An intermediate, which was obtained after reflux reaction under nitrogen atmosphere for 20 h, was cooled to room temperature, added to water, and then filtered through a diatomite pad. The filtrate was extracted with dichloromethane, then washed with water and dried over anhydrous magnesium sulfate. The crude product, obtained after filtration and evaporation, was purified through silica-gel column chromatography to obtain an intermediate product HT012-1.

In a 250 ml round bottom flask, the intermediate product HT012-1 (12 mmol), cuprous iodide (15 mmol), potassium t-butoxide (65 mmol), 1,2-diaminocyclohexane (12 mmol), and N-[1,1'-biphenyl]-3-yl-[1,1'-biphenyl]-3-amine (12 mmol) were added to dried 1,4-dioxane (100 ml), and the mixture was refluxed for 48 hours under N$_2$ atmosphere to obtain an intermediate. The obtained intermediate was cooled to room temperature, added to water, and then filtered through a diatomite pad. The filtrate was extracted with dichloromethane, then washed with water and dried over anhydrous magnesium sulfate. The crude product, obtained after filtration and evaporation, was purified through silica-gel column chromatography to obtain an aimed product HT012.

Elementary analysis results of Compound HT012 (molecular formula C$_{54}$H$_{36}$N$_2$O): theoretical: C, 88.98; H, 4.98; N, 3.84; O, 2.20. Measured: C, 88.98; H, 4.98; N, 3.84; O, 2.20. ESI-MS (m/z) (M+) analyzed by liquid chromatography-mass spectrometry: theoretical: 728.28, and measured: 728.88.

Example 3

Synthesis of Compound HT044

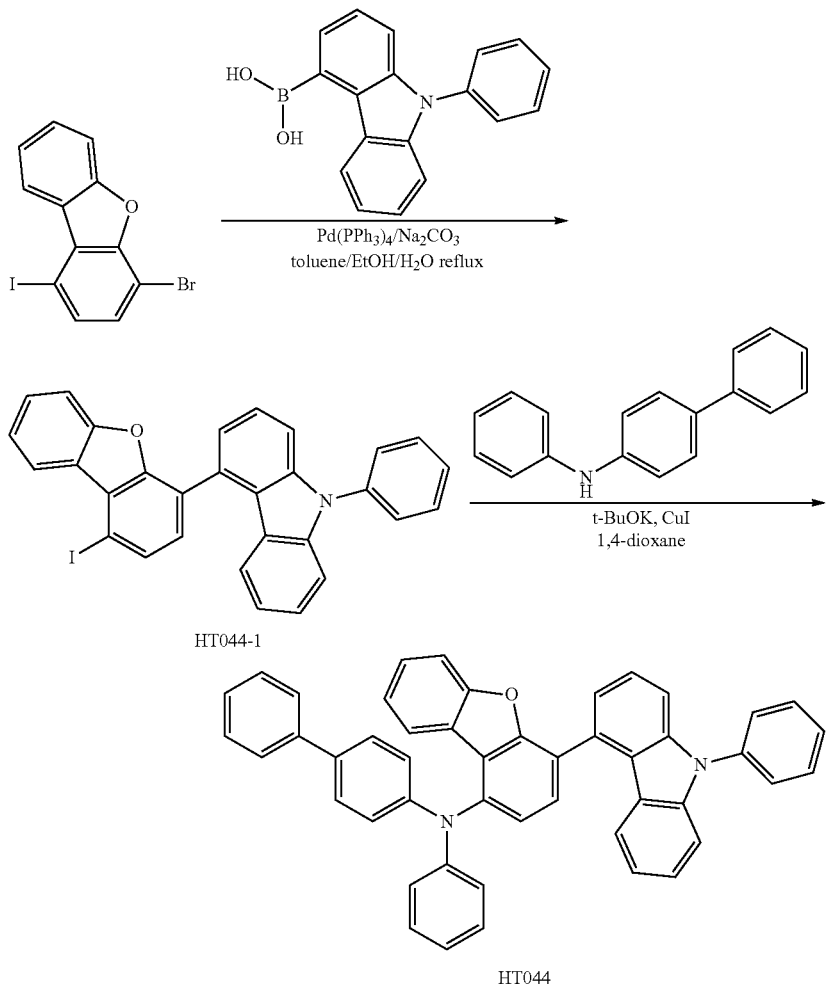

In a 250 ml round bottom flask, 1-bromo-4-iododibenzofuran (12 mmol), 4-borono-9-phenyl-carbazole (10 mmol), and Na$_2$CO$_3$ (80 mmol) were added to a solvent of toluene/EtOH (anhydrous ethanol)/H$_2$O (75/25/50, mL) to obtain a mixed solution, and then Pd(PPh$_3$)$_4$ (0.48 mmol) was added to the above mixed solution. An intermediate, which was obtained after reflux reaction under nitrogen atmosphere for 20 h, was cooled to room temperature, added to water, and then filtered through a diatomite pad. The filtrate was extracted with dichloromethane, then washed with water and dried over anhydrous magnesium sulfate. The crude product, obtained after filtration and evaporation, was purified through silica-gel column chromatography to obtain an intermediate product HT044-1.

In a 250 ml round bottom flask, the intermediate product HT044-1 (12 mmol), cuprous iodide (15 mmol), potassium t-butoxide (65 mmol), 1,2-diaminocyclohexane (12 mmol), and N-phenyl[1,1'-biphenyl]-4-amine (12 mmol) were added to dried 1,4-dioxane (100 ml), and the mixture was refluxed for 48 hours under N$_2$ atmosphere to obtain an intermediate. The obtained intermediate was cooled to room temperature, added to water, and then filtered through a diatomite pad. The filtrate was extracted with dichloromethane, then washed with water and dried over anhydrous magnesium sulfate. The crude product, obtained after filtration and evaporation, was purified through silica-gel column chromatography to obtain an aimed product HT044.

Elementary analysis results of Compound HT044 (molecular formula C$_{48}$H$_{32}$N$_2$O): theoretical: C, 88.32; H, 4.94; N, 4.29; O, 2.45. Measured: C, 88.32; H, 4.94; N, 4.29; O, 2.45. ESI-MS (m/z) (M+) analyzed by liquid chromatography-mass spectrometry: theoretical: 652.25, and measured: 652.78.

Example 4

Synthesis of Compound HT062

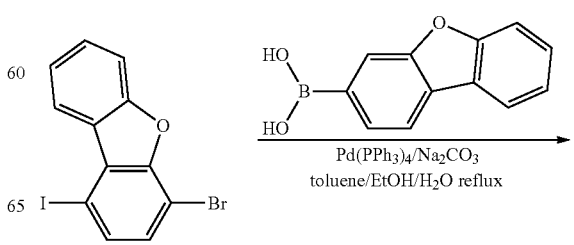

29
-continued

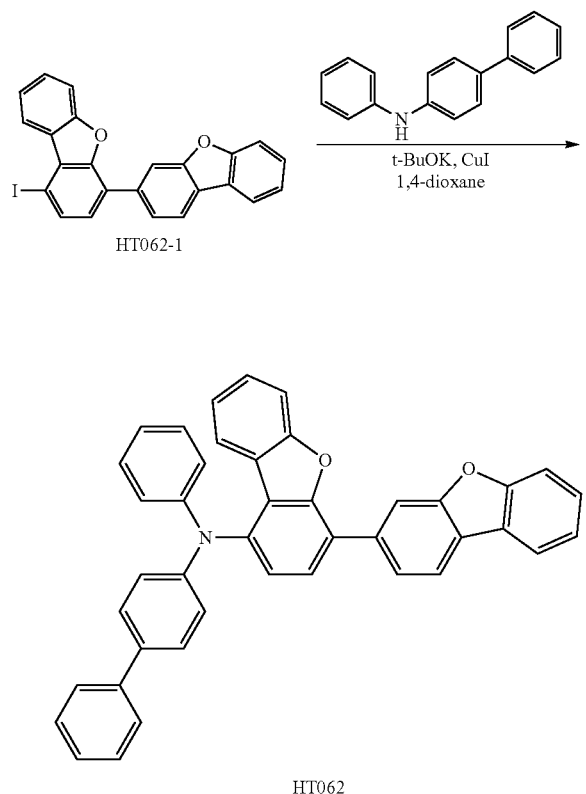

In a 250 ml round bottom flask, 1-bromo-4-iododibenzofuran (12 mmol), 2-dibenzofuranboronic acid (10 mmol), and Na$_2$CO$_3$ (80 mmol) were respectively added to a solvent of toluene/EtOH (anhydrous ethanol)/H$_2$O (75/25/50, mL) to obtain a mixed solution, and then Pd(PPh$_3$)$_4$ (0.48 mmol) was added to the above mixed solution. An intermediate, which was obtained after reflux reaction under nitrogen atmosphere for 20 h, was cooled to room temperature, added to water, and then filtered through a diatomite pad. The filtrate was extracted with dichloromethane, then washed with water and dried over anhydrous magnesium sulfate. The crude product, obtained after filtration and evaporation, was purified through silica-gel column chromatography to obtain an intermediate product HT062-1.

In a 250 ml round bottom flask, the intermediate product HT062-1 (12 mmol), cuprous iodide (15 mmol), potassium t-butoxide (65 mmol), 1,2-diaminocyclohexane (12 mmol), and N-phenyl[1,1'-biphenyl]-4-amine (12 mmol) were added to dried 1,4-dioxane (100 ml), and the mixture was refluxed for 48 hours under N$_2$ atmosphere to obtain an intermediate. The obtained intermediate was cooled to room temperature, added to water, and then filtered through a pad of diatomite. The filtrate was extracted with dichloromethane, then washed with water and dried over anhydrous magnesium sulfate. The crude product, obtained after filtration and evaporation, was purified through silica-gel column chromatography to obtain an aimed product HT062.

Elementary analysis results of HT062 (molecular formula C$_{42}$H$_{27}$NO$_2$): theoretical: C, 87.32; H, 4.71; N, 2.42; O, 5.54. Measured: C, 87.32; H, 4.72; N, 2.41; O, 5.54. ESI-MS (m/z) (M+) analyzed by liquid chromatography-mass spectrometry: theoretical: 577.20, and measured: 577.67.

30

Example 5

Synthesis of Compound HT070

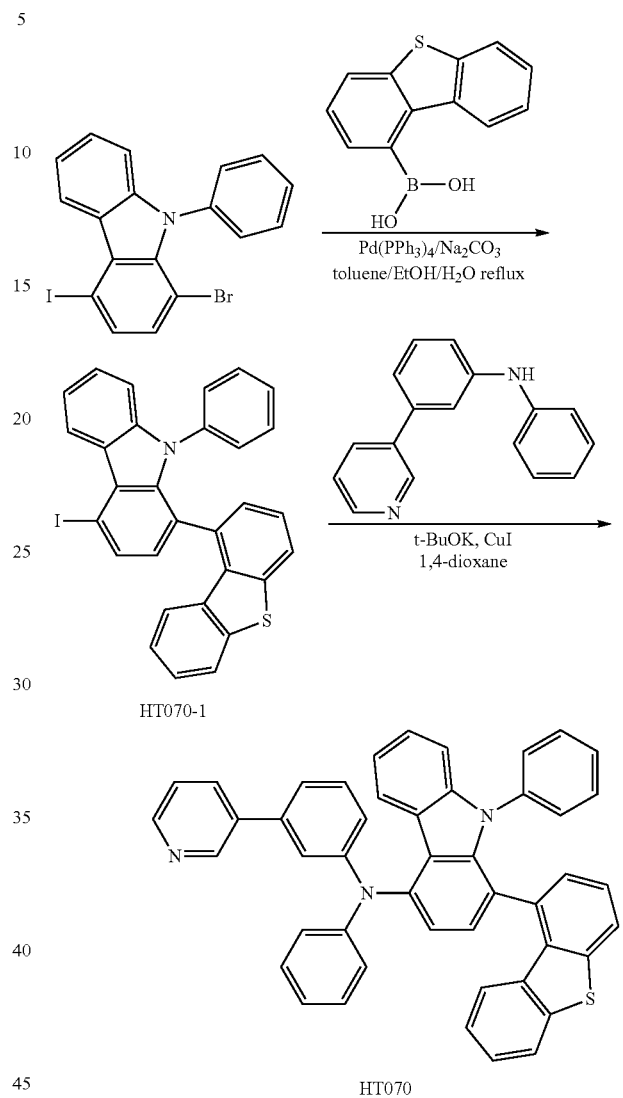

In a 250 ml round bottom flask, 1-bromo-4-iodo-9-phenyl-9H-carbazole (12 mmol), 4-dibenzothiopheneboronic acid (10 mmol), and Na$_2$CO$_3$ (80 mmol) were respectively added to a solvent of toluene/EtOH (anhydrous ethanol)/H$_2$O (75/25/50, mL) to obtain a mixed solution, and then Pd(PPh$_3$)$_4$ (0.48 mmol) was added to the above mixed solution. An intermediate, which was obtained after reflux reaction under nitrogen atmosphere for 20 h, was cooled to room temperature, added to water, and then filtered through a diatomite pad. The filtrate was extracted with dichloromethane, then washed with water and dried over anhydrous magnesium sulfate. The crude product, obtained after filtration and evaporation, was purified through silica-gel column chromatography to obtain an intermediate product HT070-1.

In a 250 ml round bottom flask, the intermediate product HT070-1 (12 mmol), cuprous iodide (15 mmol), potassium t-butoxide (65 mmol), 1,2-diaminocyclohexane (12 mmol), and N-phenyl-3-(3-pyridyl)aniline (12 mmol) were added to dried 1,4-dioxane (100 ml), and the mixture was refluxed for 48 hours under $N_2$ atmosphere to obtain an intermediate. The obtained intermediate was cooled to room temperature, added to water, and then filtered through a diatomite pad. The filtrate was extracted with dichloromethane, then washed with water and dried over anhydrous magnesium sulfate. The crude product, obtained after filtration and evaporation, was purified through silica-gel column chromatography to obtain an aimed product HT070.

Elementary analysis results of Compound HT070 (molecular formula $C_{47}H_{31}N_3S$): theoretical: C, 84.28; H, 4.66; N, 6.27; S, 4.79. Measured: C, 84.28; H, 4.67; N, 6.26; S, 4.79. ESI-MS (m/z) (M+) analyzed by liquid chromatography-mass spectrometry: theoretical: 669.22, and measured: 669.83. HOMO values, LUMO values, energy differences $E_g$, and triplet energy levels ($E_T$) of Compounds HT007, HT012, HT044, HT062 and HT070 are listed in Table 1.

TABLE 1

| Compound | HOMO (eV) | LUMO (eV) | $E_g$ (eV) | $E_T$ (eV) |
|---|---|---|---|---|
| HT007 | 5.241 | 2.170 | 3.071 | 2.816 |
| HT012 | 5.271 | 2.157 | 3.114 | 2.867 |
| HT044 | 5.208 | 2.162 | 3.046 | 2.841 |
| HT062 | 5.238 | 2.164 | 3.074 | 2.839 |
| HT070 | 5.229 | 2.172 | 3.057 | 2.853 |

It can be seen from Table 1 that the compounds of the present disclosure can be used as the hole transport material, having a suitable HOMO value and a relatively low LUMO value, thereby improving the hole transport capability. The compounds of the present disclosure can also be used as the electron blocking material to effectively enhance the electron blocking ability. Moreover, the compounds of the present disclosure have relatively high triplet energy level ($E_T$>2.8 eV), which can effectively prevent excitons from crossing the light-emitting layer and improve the light-emitting efficiency of the organic light-emitting element. Besides, the compounds of the present disclosure have excellent thermal stability and film stability, which are conducive to prolonging the service life of the organic light-emitting element.

Manufacturing of Organic Light-Emitting Element

[Element Example 1] Blue Organic Light-Emitting Element (the Compound of the Present Disclosure was Used as the Material of the Hole Ttransport Layer)

Figure 2:
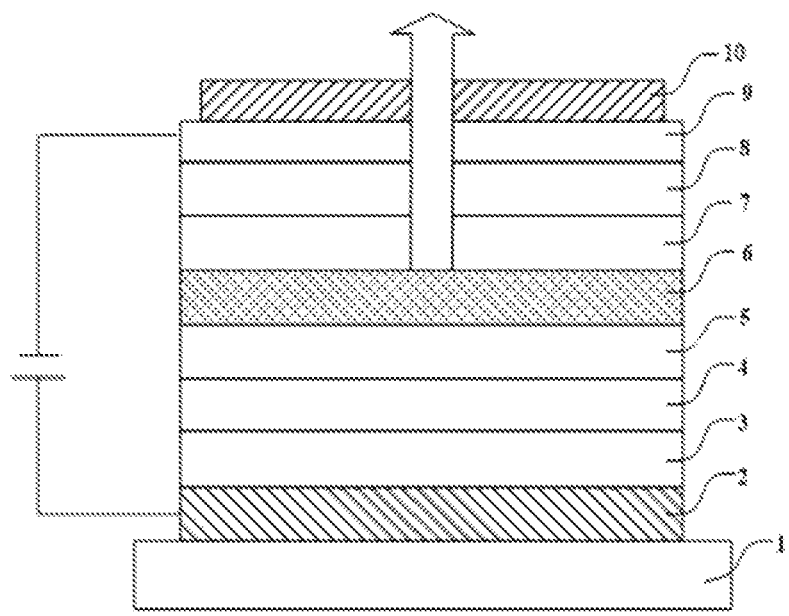
FIG. 2 is a structural schematic diagram of an OLED element according to an embodiment of the present disclosure.

This example provides an organic light-emitting element. As shown in FIG. 2, the organic light-emitting element includes: a substrate 1, an ITO anode 2, a first hole transport layer 3, a second hole transport layer 4, an electron blocking layer 5, a light-emitting layer 6, a first electron transport layer 7, a second electron transport layer 8, a cathode 9 (magnesium-silver electrode, a mass ratio of magnesium to silver is 9:1), and a capping layer (CPL) 10. Thicknesses of the layers are as follows: the ITO anode 2, 15 nm; the first hole transport layer 3, 10 nm; the second hole transport layer 4, 95 nm; the electron blocking layer 5, 90 nm; the light-emitting layer 6, 30 nm; the first electron transport layer 7, 30 nm; the second electron transport layer 8, 5 nm; the magnesium-silver cathode 9, 15 nm; and the capping layer (CPL) 10, 100 nm.

The organic light-emitting element of this example was manufactured according to the following steps:

1) A glass substrate 1 was cut into a size of 50 mm×50 mm×0.7 mm, subjected to ultrasonic treatment respectively in isopropyl alcohol and deionized water for 30 min, and then exposed to ozone for about 10 min for cleaning; the obtained glass substrate with an ITO anode 2 was mounted to a vacuum deposition apparatus;
2) A hole injection layer material, i.e., HT007 (obtained in Example 1): HAT-CN, was vacuum evaporated onto the ITO anode 2 to form a layer having a thickness of 10 nm as the first hole transport layer 3;
3) HT007 was vacuum evaporated onto the first hole transport layer 3 to form a layer having a thickness of 95 nm as the second hole transport layer 4;
4) NPB was vacuum evaporated on the hole transport layer 4 to form a layer having a thickness of 90 nm as the electron blocking layer 5;
5) CBP as a host material and Flrpic as a doping material, with a mass ratio of CBP to Flrpic of 97:3, were co-deposited on the electron blocking layer 5 to form the light-emitting layer 6 having a thickness of 30 nm;
6) Alq3 was vacuum evaporated onto the light-emitting layer 6 to form the first electron transport layer 7 having a thickness of 30 nm;
7) LiF was vacuum evaporated onto the first electron transport layer 7 to form the second electron transport layer 8 having a thickness of 5 nm;
8) Magnesium-silver was vacuum evaporated onto the second electron transport layer 8 to form the cathode 9 having a thickness of 15 nm, in which a mass ratio of Mg to Ag was 9:1; and
9) CBP, a hole material having a high refractive index, was vacuum evaporated onto the cathode 9 to obtain a cathode capping layer (CPL) having a thickness of 100 nm.

The structural formulas of the material HAT-CN, HT007, CBP, Flrpic, NPB, Alq3 mentioned in the above steps are shown as below:

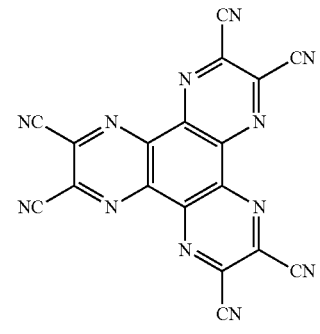

HAT-CN

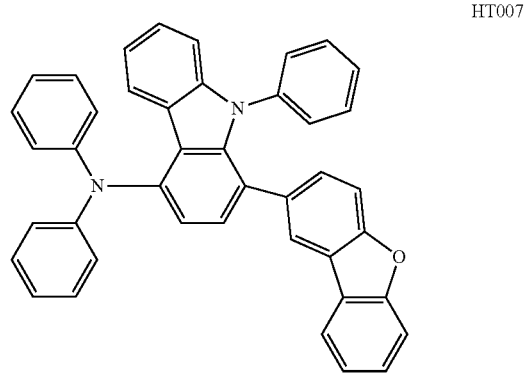

HT007

-continued

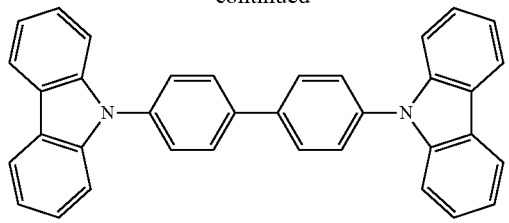
CBP

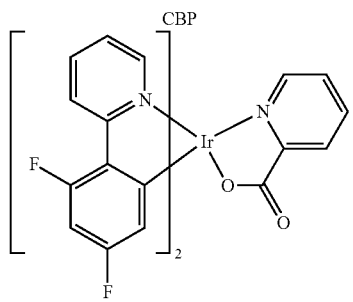
FIrpic

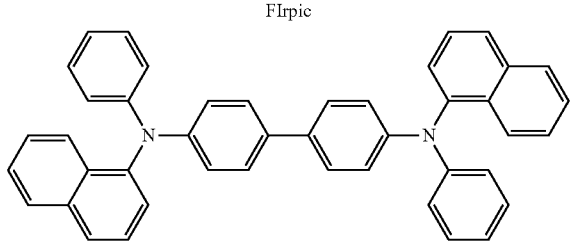
NPB

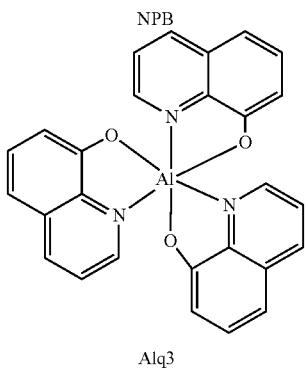
Alq3

Element Example 2

[Element Example 2] differs from [Element Example 1] in that HT007 in the first hole transport layer 3 and the second hole transport layer 4 was replaced with HT012. The materials of other layers and the manufacturing steps were the same.

Element Example 3

[Element Example 3] differs from [Element Example 1] in that HT007 in the first hole transport layer 3 and the second hole transport layer 4 was replaced with HT044. The materials of other layers and the manufacturing steps were the same.

Element Example 4

[Element Example 4] differs from [Element Example 1] in that HT007 in the first hole transport layer 3 and the second hole transport layer 4 was replaced with HT062. The materials of other layers and the manufacturing steps were the same.

Element Example 5

[Element Example 5] differs from [Element Example 1] in that HT007 in the first hole transport layer 3 and the second hole transport layer 4 was replaced with HT070. The materials of other layers and the manufacturing steps were the same.

Element Comparative Example 1

[Element Comparative Example 1] differs from [Element Example 1] in that HT007 in the first hole transport layer 3 and the second hole transport layer 4 was replaced with NPB. The materials of other layers and the manufacturing steps were the same.

TABLE 2

Test results of [Element Examples] and [Element Comparative Example 1]

| No. | Hole transport material | Driving voltage (V) | E/CIEy | Service life LT95 (hour) (at 50 mA/cm$^2$) |
|---|---|---|---|---|
| [Element Example 1] | HT007 | 3.85 | 68.4 | 65 |
| [Element Example 2] | HT012 | 3.84 | 68.7 | 65 |
| [Element Example 3] | HT044 | 3.82 | 69.4 | 66 |
| [Element Example 4] | HT062 | 3.81 | 69.1 | 67 |
| [Element Example 5] | HT070 | 3.82 | 69.5 | 66 |
| [Element Comparative Example 1] | NPB | 4.05 | 63.8 | 60 |

It can be seen from Table 2 that the light-emitting elements provided by the present disclosure have a lower driving voltage, a higher light-emitting efficiency and a longer service life, in which the driving voltages are lower than 3.85V, the light-emitting efficiencies are greater than 68Cd/A, and the service life is longer than 60 h. Compared with [Element Comparative Example 1], the voltage is increased by about 5%, the efficiency is increased by 7.5%, and the service life is prolonged by 10% or more. The above performances of the light-emitting elements are all improved significantly, which are mainly attributed to the materials of the present disclosure having a suitable HOMO value and a higher triplet energy level (>2.8 eV) matching the adjacent layers. In this way, the holes can be effectively transmitted to the light-emitting layer and effectively composited with electrons to be excited for emitting light.

Manufacturing of Organic Light-Emitting Element

[Element Example 6] Blue Organic Light-Emitting Element (the Compound of the Present Disclosure was Used as the Material of the Electron Blocking Layer)

This example provides an organic light-emitting element. The organic light-emitting element has the same structure as the Element Example 1, except that each layer thereof has a different material. As shown in FIG. 2, the organic light-emitting element includes: a substrate 1, an ITO anode 2, a first hole transport layer 3, a second hole transport layer 4, an electron blocking layer 5, a light-emitting layer 6, a first electron transport layer 7, a second electron transport layer 8, a cathode 9 (magnesium-silver electrode, a mass ratio of magnesium to silver is 9:1), and a capping layer (CPL) 10. Thicknesses of the layers are as follows: the ITO anode 2, 15 nm; the first hole transport layer 3, 10 nm; the second hole transport layer 4, 95 nm; the electron blocking layer 5, 90 nm; the light-emitting layer 6, 30 nm; the first electron transport layer 7, 30 nm; the second electron transport layer 8, 5 nm; the magnesium-silver cathode 9, 15 nm; and the capping layer (CPL) 10, 100 nm.

The organic light-emitting element of this example was manufactured according to the following steps:

1) A glass substrate 1 was cut into a size of 50 mm×50 mm×0.7 mm, subjected to ultrasonic treatment respectively in isopropyl alcohol and deionized water for 30 min, and then exposed to ozone for about 10 min for cleaning; the obtained glass substrate with an ITO anode 2 was mounted to a vacuum deposition apparatus;
2) A hole injection layer material, i.e., TAPC: HAT-CN, was vacuum evaporated onto the ITO anode 2 to form a layer having a thickness of 10 nm as the first hole transport layer 3;
3) TAPC was vacuum evaporated onto the first hole transport layer 3 to form a layer having a thickness of 95 nm as the second hole transport layer 4;
4) HT007 obtained in Example 1 was vacuum evaporated on the second hole transport layer 4 to form a layer having a thickness of 90 nm as the electron blocking layer 5;
5) CBP as a host material and FIrpic as a doping material, with a mass ratio of CBP to FIrpic of 97:3, were co-deposited on the electron blocking layer 5 to form the light-emitting layer 6 having a thickness of 30 nm;
6) Alq3 was vacuum evaporated onto the light-emitting layer 6 to form the first electron transport layer 7 having a thickness of 30 nm;
7) LiF was vacuum evaporated onto the first electron transport layer 7 to form the second electron transport layer 8 having a thickness of 5 nm;
8) Magnesium-silver was vacuum evaporated onto the second electron transport layer 8 to form the cathode 9 having a thickness of 15 nm, in which a mass ration of Mg to Ag was 9:1; and
9) CBP, a hole material having a high refractive index, was vacuum evaporated onto the cathode 9 to obtain a cathode capping layer (CPL) having a thickness of 100 nm.

The structural formulas of the materials HAT-CN, HT007, CBP, FIrpic, NPB and Alq3 mentioned in the above steps are shown as below:

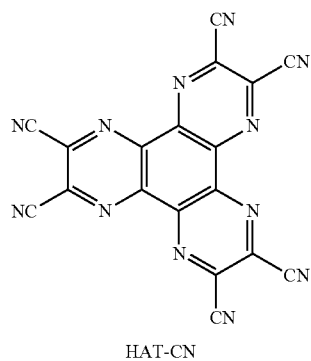

HAT-CN

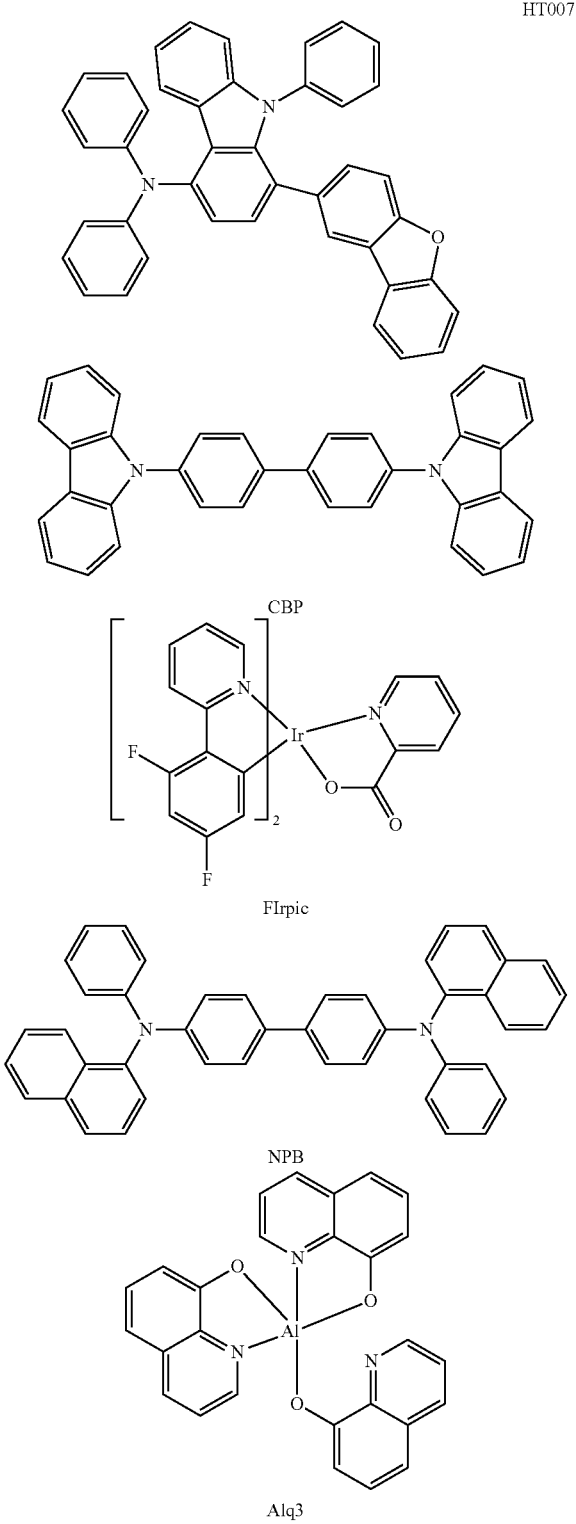

Element Example 7

[Element Example 7] differs from [Element Example 6] in that HT007 in the electron blocking layer 5 was replaced with HT012. The materials of other layers and the manufacturing steps were the same.

Element Example 8

[Element Example 8] differs from [Element Example 6] in that HT007 in the electron blocking layer 5 was replaced with HT044. The materials of other layers and the manufacturing steps were the same.

Element Example 9

[Element Example 9] differs from [Element Example 6] in that HT007 in the electron blocking layer 5 was replaced with HT062. The materials of other layers and the manufacturing steps were the same.

Element Example 10

[Element Example 10] differs from [Element Example 6] in that HT007 in the electron blocking layer 5 was replaced with HT070. The materials of other layers and the manufacturing steps were the same.

Element Comparative Example 2

[Element Comparative Example 2] differs from [Element Example 6] in that HT007 in the electron blocking layer 5 was replaced with NPB. The materials of other layers and the manufacturing steps were the same.

TABLE 3

Test results of [Element Examples] and [Element Comparative Example 2]

| No. | Materials of Eelectron blocking layer | Driving voltage (V) | E/CIEy | Service life LT95 (hour) (at 50 mA/cm$^2$) |
|---|---|---|---|---|
| [Element Example 6] | HT007 | 3.79 | 70.4 | 66 |
| [Element Example 7] | HT012 | 3.76 | 70.3 | 67 |
| [Element Example 8] | HT044 | 3.78 | 70.4 | 68 |
| [Element Example 9] | HT062 | 3.78 | 70.1 | 66 |
| [Element Example 10] | HT070 | 3.80 | 70.2 | 68 |
| [Element Comparative Example 2] | NPB | 3.98 | 65.1 | 62 |

It can be seen from Table 3 that the light-emitting elements provided by the present disclosure have a lower driving voltage, a higher light-emitting efficiency and a longer service life, in which the driving voltages are lower than 3.80V, the light-emitting efficiencies are greater than 70 Cd/A, and the service life is longer than 65 h. Compared with [Element Comparative Example 2], the voltage is increased by about 5%, the efficiency is increased by 7.5%, and the service life is prolonged by 8% or more. The above performances of the light-emitting elements are all improved significantly, which are mainly attributed to the materials of the present disclosure having a suitable HOMO value and a relatively low LUMO value matching the adjacent layers, thereby effectively preventing the electrons from crossing the light-emitting layer, and confining the electrons in the light-emitting layer to be composited with the holes. Moreover, the materials have a higher triplet energy level (>2.8 eV), which can effectively prevent back-flowing of the excitons, improve utilization of the excitons, and effectively reduce the generation of non-radiative energy.

Another aspect of the present disclosure provides a display device including the display panel described above.

Figure 3:
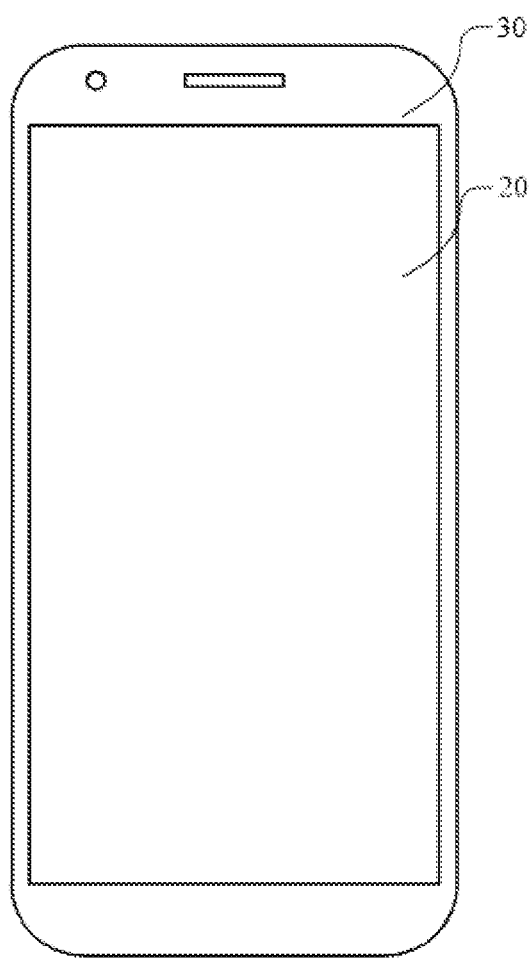
FIG. 3 is a schematic diagram of a display device according to an embodiment of the present disclosure.

In the present disclosure, the organic light-emitting element can be an OLED, which can be used in an organic light-emitting display device. The organic light-emitting display device can be a display screen of mobile phone, computer, smart watch, smart car, television, VR or AR helmet display screen, or other smart devices. FIG. 3 is a schematic diagram of a display device according to an embodiment of the present disclosure, in which the reference sign 20 denotes a mobile phone display panel, and the reference sign 30 denotes the display device.

The present disclosure is described with the preferred embodiments above. Any changes and modifications made by those skilled in the art without departing from the scope of the present disclosure shall fall within the protection scope of the present disclosure. The protection scope of the present disclosure is determined by the scope defined by the claims.

What is claimed is:

1. A compound having a general structure according to Chemical Formula 1:

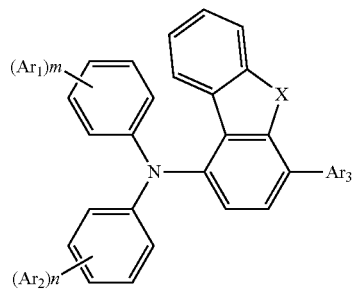

[Chemical Formula 1]

wherein Ar$_1$ and Ar$_2$ are each independently selected from the group consisting of a hydrogen atom and a substituted or unsubstituted C5-C40 heteroaryl;
m and n are each an integer independently selected from 0, 1, or 2, and m and n are not both 1;
X is —NH—;
Ar$_3$ has a structure according to Chemical Formula 2:

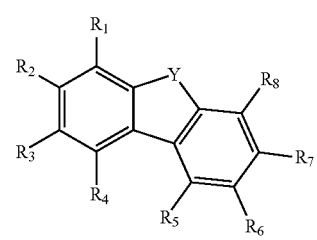

[Chemical Formula 2]

seven R7 seven of R$_1$-R$_8$ are each independently selected from the group consisting of a hydrogen atom and a substituted or unsubstituted C5-C40 aryl, and the remaining one of R$_1$-R$_8$ is a bonding position with Chemical Formula 1; and
Y is —NH—.

2. The compound according to claim 1, wherein Ar$_1$ and Ar$_2$ are each a hydrogen atom.

3. The compound according to claim 1, wherein m and n are each an integer independently selected from 0 or 1, and m and n are not both 1.

4. The compound according to claim 1, wherein seven of R$_1$-R$_8$ are each a hydrogen atom and the remaining one of R$_1$-R$_8$ is a bonding position with Chemical Formula 1.

5. The compound according to claim 1, wherein the compound has a molecular weight smaller than or equal to 1000.

6. The compound according to claim 1, wherein the compound has a triplet energy level $E_T$ greater than or equal to 2.6 eV.

7. The compound according to claim 1, wherein the compound has a glass transition temperature $T_g$ greater than or equal to 120° C.

8. A display panel comprising an organic light-emitting element,
   wherein the organic light-emitting element comprises an anode, a cathode arranged opposite to the anode, a hole transport layer, and a light-emitting layer,
   wherein the hole transport layer and the light-emitting layer are disposed between the anode and the cathode, and
   wherein a material of the hole transport layer comprises one or more compounds according to claim 1.

9. The display panel according to claim 8, further comprising an electron blocking layer disposed between the anode and the cathode,
   wherein the electron blocking layer comprises one or more compounds according to claim 1.

10. A display device comprising the display panel according to claim 8.

* * * * *